(12) United States Patent
Nii et al.

(10) Patent No.: US 6,593,013 B2
(45) Date of Patent: Jul. 15, 2003

(54) ELECTROLUMINESCENCE DEVICE, CYCLIC AZINE COMPOUND AND PRODUCTION PROCESS OF CYCLIC AZINE DYE

(75) Inventors: Kazumi Nii, Kanagawa (JP); Tatsuya Igarashi, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 10/041,450

(22) Filed: Jan. 10, 2002

(65) Prior Publication Data

US 2002/0102435 A1 Aug. 1, 2002

Related U.S. Application Data

(62) Division of application No. 09/179,837, filed on Oct. 28, 1998, now Pat. No. 6,379,823.

(30) Foreign Application Priority Data

Oct. 28, 1997 (JP) .............................. 9-295563
Nov. 17, 1997 (JP) .............................. 9-315249
Jun. 26, 1998 (JP) ............................ 10-180870

(51) Int. Cl.[7] .............................. H05B 33/12
(52) U.S. Cl. ................ 428/690; 428/917; 313/504; 313/506
(58) Field of Search ................ 428/690, 704, 428/917; 313/504, 506

(56) References Cited

U.S. PATENT DOCUMENTS 5,281,489 A   1/1994   Mori et al. ................ 428/690

FOREIGN PATENT DOCUMENTS

| EP | 0 765 106 A2 | 3/1997 |
| JP | 7-211457 | 8/1995 |
| JP | 8-298186 | 11/1996 |

OTHER PUBLICATIONS

Machine–assisted translation of JP 7–211457 (Aug. 1995).*

* cited by examiner

*Primary Examiner*—Marie Yamnitzky
(74) *Attorney, Agent, or Firm*—Sughrue Mion, PLLC

(57) ABSTRACT

An organic electroluminescence device including at least one organic thin film between electrodes, which contains at least one compound represented by the following formula (1):

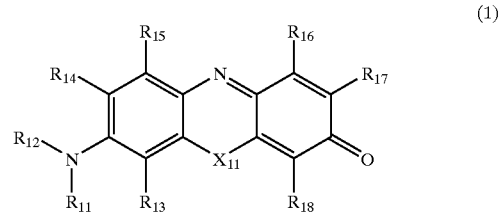

wherein $X_{11}$ represents a sulfur atom or N—$R_{19}$, and $R_{11}$ to $R_{18}$ and $R_{19}$, which may be the same or different, each represents a hydrogen atom or a substituent, provided that $R_{16}$ and $R_{17}$ are not combined to form an aromatic ring.

3 Claims, No Drawings

ELECTROLUMINESCENCE DEVICE, CYCLIC AZINE COMPOUND AND PRODUCTION PROCESS OF CYCLIC AZINE DYE

This is a divisional of application Ser. No. 09/179,837 filed Oct. 28, 1998, now U.S. Pat. No. 6,379,823; the disclosure of which is incorporated herein by reference.

FIELD OF THE INVENTION

The present invention relates to a cyclic azine dye and an electroluminescence (EL) device using the same.

BACKGROUND OF THE INVENTION

At the present time, development and study on various display devices are aggressively driven. In particular, organic EL devices can obtain high luminance light emission at a low voltage and accordingly, are drawing an attention as a promising display device. For example, an EL device comprising an organic thin film formed by depositing an organic compound is known (see, Applied Physics Letters, Vol. 51, page 913 (1987)). The organic EL device described in this publication has a laminate structure comprising an electron transporting material and a hole transporting material and is greatly improved in the light emission properties as compared with conventional single-layer devices.

As a means to improve the light emission efficiency of the laminate-type EL device, a method of doping a fluorescent dye is known. For example, an organic EL device having doped therein a coumarin dye described in Journal of Applied Physics, Vol. 65, page 3,610 (1989) is greatly improved in the light emission efficiency as compared with non-doped devices.

Furthermore, by doping a fluorescent dye, light having a desired wavelength can be taken out. In order to apply the organic EL device to a full color display or back light, a fluorescent dye capable of emitting light at an appropriate wavelength and having excellent durability must be developed, in particular, a red fluorescent dye is being demanded in view of durability and light emission efficiency.

As the red fluorescent dye used in the organic electroluminescence device, 4-(dicyanomethylene)-2-methyl-6-(4-dimethylaminostyryl)-4H-pyrane (DCM), for example, is doped and thereby emission of red orange light is obtained, however, this dye has problems that the color purity is low and the durability is poor, and cannot be used in practice. Neil Red is also known, however, this is still disadvantageous in that the color hue is short wave and the durability is not sufficiently high. In the same way, various EL devices which can emit light at a longer wavelength than the green light as a result of doping a fluorescent material have been developed, however, these devices all have serious problems that the color purity is low as red color light emission and the luminance of emitted light is not sufficiently high. EL devices using a conventional red fluorescent dye have another problem that the durability is low. Furthermore, with respect to a fluorescent dye which emits light in the blue green area, dyes capable of emitting light with excellent luminance and having superior durability have not yet been developed and a new dye is being demanded.

Of organic EL devices, devices in which an organic material is laminated by vacuum deposition can successfully achieve high luminance light emission, however, in view of simplification of the production process, workability and the like or for obtaining a large area, the device is preferably fabricated by a coating method. The devices fabricated by the conventional coating method are, however, inferior in the luminance of emitted light and the light emission efficiency to the devices fabricated by the deposition method. Thus, improvements are still in need for attaining high luminance and highly efficient light emission.

SUMMARY OF THE INVENTION

A first object of the present invention is to provide an organic EL device using a red fluorescent dye capable of emitting red light in high color purity and having excellent durability.

A second object of the present invention is to provide a red fluorescent dye which can be used in an organic EL device, emits red light in high color purity and has excellent durability.

A third object of the present invention is to provide an organic EL device which can ensure high luminance and highly efficient light emission even when the device is fabricated by a coating method.

A fourth object of the present invention is to provide an organic EL device using a fluorescent dye capable of emitting light in the blue green area and having excellent durability.

The present invention provides the following electroluminescence devices and fluorescent dyes and thereby the above-described objects of the present invention can be attained.

[1] An organic electroluminescence device comprising at least one organic thin film between electrodes, which contains at least one compound represented by the following formula (1), (2) or (3):

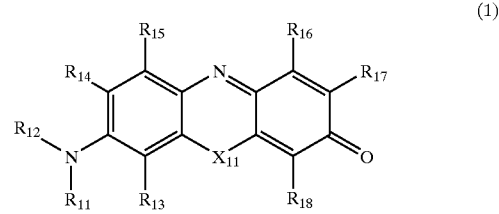

(1)

wherein $X_{11}$ represents an oxygen atom, a sulfur atom or N—$R_{19}$, and $R_{11}$ to $R_{18}$ and $R_{19}$, which may be the same or different, each represents a hydrogen atom or a substituent, provided that $R_{16}$ and $R_{17}$ are not combined to form an aromatic ring;

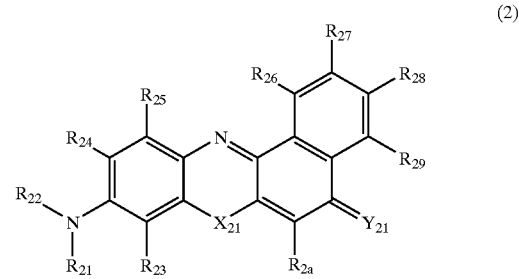

(2)

wherein $X_{21}$ represents an oxygen atom, a sulfur atom or N—$R_{2b}$, $Y_{21}$ represents an oxygen atom or a sulfur atom, and $R_{21}$ to $R_{29}$ and $R_{2b}$, which may be the same or different, each represents a hydrogen atom or a substituent, and $R_{2a}$ represents a hydrogen atom, an alkyl group, an alkenyl group, an alkynyl group, an aryl group, a heterocyclic group, an unsubstituted amino group, an acylamino group, a sulfonyl-amino group, a carbamoylamino group, a sulfamoylamino group, an alkoxycarbonylamino group, an aryloxycarbonylamino group, a phosphoramido group, an acyl group, a carbamoyl group, a sulfonyl group, a sulfamoyl group, a cyano group or a halogen atom, provided that when $X_{21}$ represents an oxygen atom and $R_{29}$ represents a hydrogen atom, at least one of $R_{26}$ to $R_{29}$ represents an unsubstituted or substituted amino group;

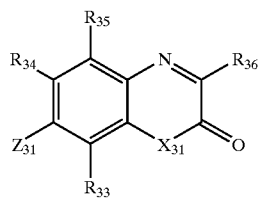

(3)

wherein $X_{31}$, represents an oxygen atom, a sulfur atom or N—$R_{3b}$, $Z_{31}$, represents $NR_{31}R_{32}$ or $OG_{31}$, $R_{31}$ to $R_{36}$ and $R_{3b}$ each represents a hydrogen atom or a substituent, and $G_{31}$ represents a hydrogen atom, a substituent or a counter cation group.

[2] A cyclic azine compound having a structure represented by the following formula (4):

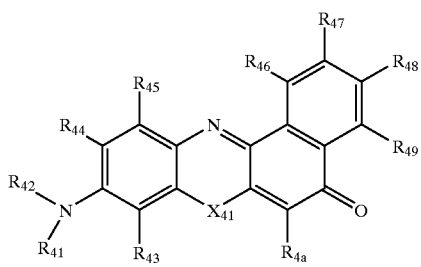

(4)

wherein $X_{41}$ represents an oxygen atom, a sulfur atom or N—$R_{4b}$, $R_{4b}$ represents a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_4$, and $R_{42}$ each represents a substituted or unsubstituted alkyl group having from 1 to 20 carbon atoms or an aryl group having from 6 to 20 carbon atoms, $R_{43}$, $R_{44}$ and $R_{45}$ each represents a hydrogen atom, a substituted or unsubstituted alkyl group having from 1 to 20 carbon atoms, a halogen atom, a hydroxy group, a substituted or unsubstituted alkoxy group having from 1 to 20 carbon atoms, an unsubstituted amino group, a substituted amino group having from 1 to 20 carbon atoms, the substituted amino group being an alkylamino group, an arylamino group, a sulfonamido group, a carbonamido group, a ureido group, a urethane group, a carbamoylamino group or a sulfamoylamino group, $R_{46}$, $R_{47}$, $R_{48}$ and $R_{49}$ each represents a hydrogen atom, a halogen atom, a substituted carbonyl group having from 1 to 30 carbon atoms, an alkylamino group having from 1 to 30 carbon atoms, an arylamino group having from 6 to 30 carbon atoms a sulfonylamino group having from 1 to 30 carbon atoms, an acylamino group having from 2 to 30 carbon atoms, a ureido group having from 1 to 30 carbon atoms, an alkoxycarbonylamino group having from 2 to 30 carbon atoms, an aryloxycarbonylamino group having from 7 to 30 carbon atoms, a carbamoylamino group having from 1 to 30 carbon atoms or a sulfamoylamino group having from 1 to 30 carbon atoms, and $R_{4a}$ represents a hydrogen atom, a cyano group, a substituted carbonyl group having from 1 to 30 carbon atoms, a sulfamoyl group having from 0 to 30 carbon atoms, a sulfonyl group having from 1 to 30 carbon atoms, a sulfonamido group having from 1 to 30 carbon atoms, a carbonamido group having from 1 to 30 carbon atoms or a ureido group having from 1 to 30 carbon atoms, provided that when $X_{41}$ is an oxygen atom and $R_{4a}$, represents a hydrogen atom or a cyano group, at least one of $R_{46}$ to $R_{49}$ represents a substituted amino group and when $X_{41}$ represents a sulfur atom, $R_{4a}$ represents a hydrogen atom, a cyano group or a sulfamoyl group, the substituent of the substituted carbonyl group being an alkyl group, an aryl group, a heterocyclic group, an alkoxy group, an aryloxy group, an arylamino group or an alkylamino group.

[3] An organic electroluminescence device comprising a pair of electrodes having formed therebetween a light emitting layer or a plurality of organic compound thin films including a light emitting layer, wherein at least one layer is a layer comprising a polymer having dispersed therein a compound represented by formula (1), (2), (3) or (4) described in the above items [1] and [2].

[4] An organic electroluminescence device comprising a pair of electrodes having formed therebetween a light emitting layer or a plurality of organic compound thin film including a light emitting layer, wherein at least one layer is a layer formed by coating a compound represented by formula (1), (2), (3) or (4) described in the above items [1] and [2] or a material containing the compound.

[5] A process for producing a cyclic azine dye represented by the following formula (15), comprising reacting a phenylenediamine derivative represented by the following formula (13) with a phenol derivative represented by the following formula (14) in the presence of an oxidizing agent in an alkaline atmosphere:

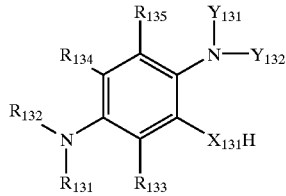

(13)

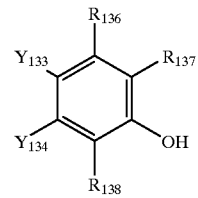

(14)

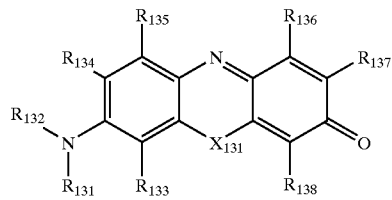

(15)

wherein $X_{131}$, represents an oxygen atom, a sulfur atom or N—$R_{139}$, $R_{131}$ to $R_{135}$ and $R_{139}$, which may be the same or different, each represents a hydrogen atom or a substituent, $R_{136}$ to $R_{138}$, which may be the same or different, each represents a hydrogen atom or a substituent, and $Y_{131}$ to $Y_{134}$, which may be the same or different, each represents a hydrogen atom or a splitting-off group.

[6] A process for producing a cyclic azine dye represented by the following formula (18), comprising oxidation reacting an aniline derivative represented by formula (16) or (17) by an oxidizing agent in an alkaline atmosphere:

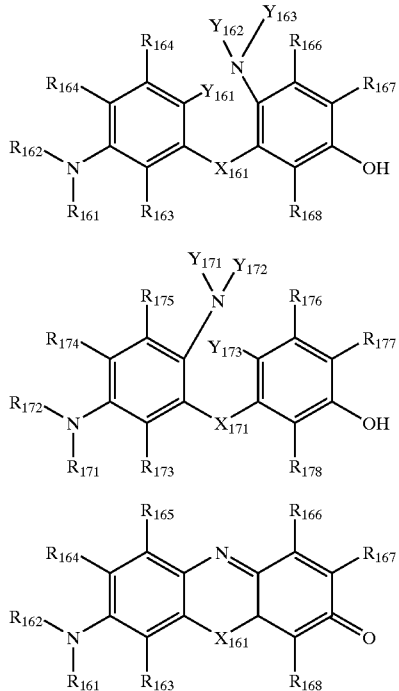

wherein $X_{161}$ represents an oxygen atom, a sulfur atom or N—$R_{169}$, $R_{161}$ to $R_{168}$ and $R_{169}$, which may be the same or different, each represents a hydrogen atom or a substituent, $X_{171}$ represents an oxygen atom, a sulfur atom or N—$R_{179}$, $R_{171}$ to $R_{178}$ and $R_{179}$, which may be the same or different each represents a hydrogen atom or a substituent, and $Y_{161}$ to $Y_{163}$ and $Y_{171}$ to $Y_{173}$, which may be the same or different, each represents a hydrogen atom or a splitting-off group.

[7] A process for producing a cyclic azine dye represented by formula (3), comprising reacting a carbonyl compound derivative represented by the following formula (19) with an aniline compound derivative represented by the following formula (20) or a salt thereof in the presence of an oxidizing agent in an alkaline atmosphere:

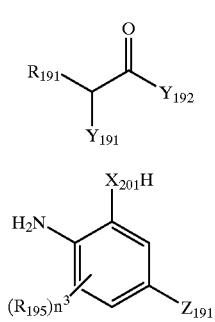

wherein $X_{201}$ represents an oxygen atom, a sulfur atom or >N$R_{192}$, $R_{192}$ represents a hydrogen atom or a substituent, $R_{191}$ represents a hydrogen atom or a substituent, $Y_{191}$ and $Y_{192}$, which may be the same or different, each represents a hydrogen atom or a splitting-off group, $Z_{191}$ represents —N$R_{193}R_{194}$ or —O$G_{191}$, $R_{193}$ and $R_{194}$, which may be the same or different, each represents a hydrogen atom or a substituent, $G_{191}$ represents a hydrogen atom, a substituent or a counter cation group, $R_{195}$ represents a substituent, and $n^3$ represents 0 or an integer of from 1 to 3, provided that when $n^3$ is 2 or 3, the plurality of $R_{195}$ groups may be the same or different.

DETAILED DESCRIPTION OF THE INVENTION

The present invention is described in detail below.

Formula (1) is described below. $X_{11}$ represents an oxygen atom, a sulfur atom or N—$R_{19}$, preferably an oxygen atom or N—$R_{19}$. $R_{19}$ represents a hydrogen atom or a substituent.

Examples of the substituent include an alkyl group preferably having from 1 to 20 carbon atoms, more preferably from 1 to 12 carbon atoms, still more preferably from 1 to 8 carbon atoms, such as methyl, ethyl, iso-propyl, tert-butyl, n-octyl, n-decyl, n-hexadecyl, cyclopropyl, cyclopentyl and cyclohexyl; an alkenyl group preferably having from 2 to 20 carbon atoms, more preferably from 2 to 12 carbon atoms, still more preferably from 2 to 8 carbon atoms, such as vinyl, allyl, 2-butenyl and 3-pentenyl; an alkynyl group preferably having from 2 to 20 carbon atoms, more preferably from 2 to 12 carbon atoms, still more preferably from 2 to 8 carbon atoms, such as propargyl and 3-pentynyl; an aryl group preferably having from 6 to 30 carbon atoms, more preferably from 6 to 20 carbon atoms, still more preferably from 6 to 12 carbon atoms, such as phenyl, p-methylphenyl and naphthyl; an acyl group preferably having from 1 to 20 carbon atoms, more preferably from 1 to 16 carbon atoms, still more preferably from 1 to 12 carbon atoms, such as acetyl, benzoyl, formyl and pivaloyl; an alkoxycarbonyl group preferably having from 2 to 20 carbon atoms, more preferably from 2 to 16 carbon atoms, still more preferably from 2 to 12 carbon atoms, such as methoxycarbonyl and ethoxycarbonyl; an aryloxycarbonyl group preferably having from 7 to 20 carbon atoms, more preferably from 7 to 16 carbon atoms, still more preferably from 7 to 10 carbon atoms, such as phenyloxycarbonyl; an alkylaminocarbonyl group preferably having from 1 to 40 carbon atoms, more preferably from 1 to 30 carbon atoms, still more preferably from 1 to 25 carbon atoms, such as ethylaminocarbonyl and dimethylaminocarbonyl; an arylaminocarbonyl group preferably having from 7 to 40 carbon atoms, more preferably from 7 to 30 carbon atoms, still more preferably from 7 to 10 carbon atoms, such as phenylaminocarbonyl; a sulfonyl group preferably having from 1 to 20 carbon atoms, more preferably from 1 to 16 carbon atoms, still more preferably from 1 to 12 carbon atoms, such as mesyl and tosyl; and a heterocyclic group, preferably a heterocyclic group having a 5- or 6-membered monocyclic or condensed ring structure and having from 3 to 30 carbon atoms (the hetero atom is, for example, oxygen, nitrogen or sulfur), such as imidazolyl, pyridyl, furyl, piperidyl and morpholino.

These substituents each may further be substituted.

$R_{19}$ may be combined with $R_{13}$ or $R_{18}$ to form a 5- or 6-membered nitrogen-containing heterocyclic ring having from 3 to 20 carbon atoms.

$R_{19}$ is preferably a hydrogen atom, a substituted or unsubstituted alkyl group having from 1 to 20 carbon atoms, a substituted carbonyl group having from 1 to 20 carbon atoms or a substituted sulfonyl group having from 1 to 20 carbon atoms. The substituent of the substituted carbonyl group is an aliphatic group, an aryl group, a heterocyclic group, an alkoxy group, an aryloxy group, a heterocyclic oxy group, an unsubstituted or substituted amino group or a hydroxyl group. The substituent of the substituted sulfonyl group is an aliphatic group, an aryl group, an alkoxy group, a substituted or unsubstituted amino group or a hydroxyl group. The substituted amino group is an alkylamino group, an arylamino group, a sulfonamido group, a carbonamido group, a ureido group, a urethane group, a carbamoylamino group or a sulfamoylamino group. $R_{19}$ is particularly preferably a hydrogen atom or an alkyl group having from 1 to 10 carbon atoms.

$R_{11}$ to $R_{18}$, which may be the same or different, each represents a hydrogen atom or a substituent.

Examples of the substituents of $R_{11}$ and $R_{12}$ include the substituents described above for $R_{19}$.

Examples of the substituent of $R_{13}$ to $R_{18}$ include an alkyl group (preferably having from 1 to 30 carbon atoms, more preferably from 1 to 20 carbon atoms, still more preferably from 1 to 12 carbon atoms, e.g., methyl, ethyl, iso-propyl, tert-butyl, n-octyl, n-decyl, n-hexadecyl, cyclopropyl, 2-ethylhexyl, cyclopentyl, cyclohexyl, trifluoromethyl, pentafluoromethyl), an alkenyl group (preferably having from 2 to 30 carbon atoms, more preferably from 2 to 20 carbon atoms, still more preferably from 2 to 12 carbon atoms, e.g., vinyl, allyl, 2-butenyl, 3-pentenyl), an alkynyl group (preferably having from 2 to 30 carbon atoms, more preferably from 2 to 20 carbon atoms, still more preferably from 2 to 12 carbon atoms, e.g., propargyl, 3-pentynyl), an aryl group (preferably having from 6 to 30 carbon atoms, more preferably from 6 to 20 carbon atoms, still more preferably from 6 to 12 carbon atoms, e.g., phenyl, p-methylphenyl, naphthyl, pentafluorophenyl), an unsubstituted amino group, an alkyl-substituted or aryl-substituted amino group (preferably having from 1 to 30 carbon atoms, more preferably from 1 to 20 carbon atoms, still more preferably from 1 to 12 carbon atoms, e.g., amino, methylamino, dimethylamino, diethylamino, dibenzylamino, anilino), an alkoxy group (preferably having from 1 to 30 carbon atoms, more preferably from 1 to 20 carbon atoms, still more preferably from 1 to 12 carbon atoms, e.g., methoxy, ethoxy, butoxy), an aryloxy group (preferably having from 6 to 30 carbon atoms, more preferably from 6 to 20 carbon atoms, still more preferably from 6 to 12 carbon atoms, e.g., phenyloxy, 2-naphthyloxy), an acyl group (preferably having from 1 to 30 carbon atoms, more preferably from 1 to 20 carbon atoms, still more preferably from 1 to 12 carbon atoms, e.g., acetyl, benzoyl, formyl, pivaloyl), an alkoxycarbonyl group (preferably having from 2 to 30 carbon atoms, more preferably from 2 to 20 carbon atoms, still more preferably from 2 to 12 carbon atoms, e.g., methoxycarbonyl, ethoxycarbonyl), an aryloxycarbonyl group (preferably having from 7 to 30 carbon atoms, more preferably from 7 to 20 carbon atoms, still more preferably from 7 to 12 carbon atoms, e.g., phenyloxycarbonyl), an alkylaminocarbonyl group (preferably having from 2 to 40 carbon atoms, more preferably from 2 to 30 carbon atoms, still more preferably from 2 to 25 carbon atoms, e.g., ethylaminocarbonyl, dimethylaminocarbonyl), an arylaminocarbonyl group (preferably having from 7 to 40 carbon atoms, more preferably from 7 to 30 carbon atoms, still more preferably from 7 to 12 carbon atoms, e.g., phenylaminocarbonyl), an acyloxy group (preferably having from 2 to 30 carbon atoms, more preferably from 2 to 20 carbon atoms, still more preferably from 2 to 12 carbon atoms, e.g., acetoxy, benzoyloxy), an acylamino group (preferably having from 2 to 30 carbon atoms, more preferably from 2 to 20 carbon atoms, still more preferably from 2 to 12 carbon atoms, e.g., acetylamino, benzoylamino), an alkoxycarbonylamino group (preferably having from 2 to 30 carbon atoms, more preferably from 2 to 20 carbon atoms, still more preferably from 2 to 12 carbon atoms, e.g., methoxycarbonylamino), an aryloxycarbonylamino group (preferably having from 7 to 30 carbon atoms, more preferably from 7 to 20 carbon atoms, still more preferably from 7 to 12 carbon atoms, e.g., phenyloxycarbonylamino), a sulfonylamino group (preferably having from 1 to 30 carbon atoms, more preferably from 1 to 20 carbon atoms, still more preferably from 1 to 12 carbon toms, e.g., methane-sulfonylamino, benzenesulfonylamino), a sulfamoyl group (preferably having from 0 to 30 carbon atoms, more preferably from 0 to 20 carbon atoms, still more preferably from 0 to 12 carbon atoms, e.g., sulfamoyl, methylsulfamoyl, dimethylsulfamoyl, phenylsulfamoyl), a carbamoyl group (preferably having from 1 to 30 carbon atoms, more preferably from 1 to 20 carbon atoms, still more preferably from 1 to 12 carbon atoms, e.g., carbamoyl, methylcarbamoyl, diethylcarbamoyl, phenylcarbamoyl), a carbamoylamino group (preferably having from 1 to 30 carbon atoms, more preferably from 1 to 20 carbon atoms, still more preferably from 1 to 12 carbon atoms, e.g., carbamoylamino, ethylcarbamoylamino, dimethylcarbamoylamino, phenylcarbamoylamino), a sulfamoylamino group (preferably having from 0 to 30 carbon atoms, more preferably from 0 to 20 carbon atoms, still more preferably from 0 to 12 carbon atoms, e.g., sulfamoylamino, methylsulfamoylamino, diethylsulfamoylamino, phenylsulfamoylamino), an alkylthio group (preferably having from 1 to 30 carbon atoms, more preferably from 1 to 20 carbon atoms, still more preferably from 1 to 12 carbon atoms, e.g., methylthio, ethylthio), an arylthio group (preferably having from 6 to 30 carbon atoms, more preferably from 6 to 20 carbon atoms, still more preferably from 6 to 12 carbon atoms, e.g., phenylthio), a sulfonyl group (preferably having from 1 to 30 carbon atoms, more preferably from 1 to 20 carbon atoms, still more preferably from 1 to 12 carbon atoms, e.g., mesyl, tosyl), a sulfinyl group (preferably having from 1 to 30 carbon atoms, more preferably from 1 to 20 carbon atoms, still more preferably from 1 to 12 carbon atoms, e.g., methanesulfinyl, benzenesulfinyl), a ureido group (preferably having from 1 to 30 carbon atoms, more preferably from 1 to 20 carbon atoms, still more preferably from 1 to 12 carbon atoms, e.g., ureido, methylureido, phenylureido), a phosphoramido group (preferably having from 1 to 30 carbon atoms, more preferably from 1 to 20 carbon atoms, still more preferably from 1 to 12 carbon atoms, e.g., diethylphosphoramido, phenylphosphoramido), a hydroxy group, a mercapto group, a halogen atom (e.g., fluorine, chlorine, bromine, iodine), a cyano group, a sulfo group, a carboxyl group, a nitro group, a hydroxamic acid group, a sulfino group, a hydrazino group, an imino group and a heterocyclic group (preferably having from 1 to 30 carbon atoms, more preferably from 1 to 20 carbon atoms; the hetero atom is, for example, a nitrogen atom, an oxygen atom or a sulfur atom; specific examples include imidazolyl, benzimidazolyl, benzoxazolyl, thiazolyl, benzothiazolyl, pyridyl, furyl, piperidyl and morpholino). These substituents each may further be substituted.

Any of the substituents $R_{13}$ to $R_{18}$ may be combined to form a 5- or 6-membered alicyclic, heterocyclic or aromatic ring, provided that $R_{16}$ and $R_{17}$ are not combined to form an aromatic ring.

$R_{11}$ and $R_{12}$ each is preferably a substituted or unsubstituted alkyl group having from 1 to 20 carbon atoms or an aryl group having from 6 to 20 carbon atoms. $R_{11}$ and $R_{12}$ may combine with $R_{13}$ or $R_{14}$, respectively, to form a 5- or 6-membered alicyclic ring, for example, an indoline ring, a tetrahydroquinoline ring or a Julolidine ring. $R_{11}$ and $R_{12}$ may be combined to form a ring, for example, a pyrrolidine ring, a piperidine ring or a morpholine ring.

$R_{13}$, $R_{14}$ and $R_{15}$ each is preferably a hydrogen atom, a substituted or unsubstituted alkyl group having from 1 to 20 carbon atoms, a halogen atom, a hydroxy group, a substituted or unsubstituted alkoxy group having from 1 to 20 carbon atoms, an unsubstituted amino group or a substituted amino group having from 1 to 20 carbon atoms. The substituted amino group is an alkylamino group, an arylamino group, an aromatic heterocyclic amino group, a sulfonamido group, a carbonamido group, a ureido group, a urethane group, a carbamoylamino group or a sulfamoylamino group.

$R_{13}$, $R_{14}$ and $R_{15}$ each is more preferably a hydrogen atom, a substituted or unsubstituted alkyl group having from 1 to 10 carbon atoms, a substituted or unsubstituted alkoxy group having from 1 to 10 carbon atoms or a substituted amino group having from 1 to 10 carbon atoms. The substituted amino group is an alkylamino group, an arylamino group, an aromatic heterocyclic amino group, a sulfonamido group, a carbonamido group, a ureido group, a urethane group, a carbamoylamino group or a sulfamoylamino group.

$R_{16}$ and $R_{17}$ each is preferably a hydrogen atom, a halogen atom, a sulfonamido group having from 1 to 30 carbon atoms, a carbonamido group having from 1 to 30 carbon atoms or a ureido group having from 1 to 30 carbon atoms. $R_{18}$ is preferably a hydrogen atom, a halogen atom, a cyano group, an alkyl group having from 1 to 30 carbon atoms, an aryl group having from 6 to 30 carbon atoms, a heterocyclic group having from 2 to 30 carbon atoms, a substituted carbonyl group having from 1 to 30 carbon atoms, a sulfamoyl group having from 0 to 30 carbon atoms, a sulfonamido group having from 1 to 30 carbon atoms, a carbonamido group having from 1 to 30 carbon atoms or a ureido group having from 1 to 30 carbon atoms, more preferably a hydrogen atom, a halogen atom, a substituted carbonyl group having from 1 to 30 carbon atoms or an amido group having from 1 to 30 carbon atoms.

The preferred combination in formula (1) is described below.

In formula (1), preferred is the combination such that $X_{11}$ is an oxygen atom or N—$R_{19}$, $R_{19}$ is a substituted or unsubstituted alkyl group having from 1 to 20 carbon atoms, a substituted carbonyl group having from 1 to 20 carbon atoms or a substituted sulfonyl group having from 0 to 20 carbon atoms, the substituent of the substituted carbonyl group is an aliphatic group, an aryl group, a heterocyclic group, an alkoxy group or an aryloxy group, the substituent of the substituted sulfonyl group is an aliphatic group or aryl group, $R_{11}$ and $R_{12}$ each is an unsubstituted or substituted alkyl group having from 1 to 20 carbon atoms or an aryl group having from 6 to 20 carbon atoms and may combine with $R_{13}$ or $R_{14}$, respectively to form a ring (preferably a 5- or 6-membered alicyclic ring), for example, an indoline ring, a tetrahydroquinoline ring or a Julolidine ring, or $R_{11}$ and $R_{12}$ may be combined with each other to form a ring, for example, a pyrrolidine ring, a piperidine ring or a morpholine ring, $R_{13}$, $R_{14}$ and $R_{15}$ each is a hydrogen atom, a substituted or unsubstituted alkyl group having from 1 to 20 carbon atoms, a halogen atom or a substituted or unsubstituted alkoxy group having from 1 to 20 carbon atoms, $R_{16}$ and $R_{17}$ each is a hydrogen atom, a halogen atom, a sulfonylamino group having from 1 to 20 carbon atoms, an acylamino group having from 2 to 20 carbon atoms or an ureido group having from 1 to 20 carbon atoms, and $R_1$ is a hydrogen atom, a halogen atom, a cyano group, a substituted carbonyl group having from 1 to 20 carbon atoms, a sulfamoyl group having from 0 to 20 carbon atoms, a sulfonylamino group having from 1 to 20 carbon atoms, an acylamino group having from 1 to 20 carbon atoms or a ureido group having from 1 to 20 carbon atoms.

Formula (2) is described below.

$X_{21}$ represents an oxygen-atom, a sulfur atom or N—$R_{2b}$, preferably an oxygen atom or N—$R_{2b}$. Examples and preferred range of $R_{2b}$ are the same as those of $R_{19}$ in formula (1). $Y_{21}$ represents an oxygen atom or a sulfur atom, preferably an oxygen atom. Examples and preferred range of $R_{21}$ to $R_{25}$ are the same as those of $R_{11}$ to $R_{15}$ in formula (1). Examples of the substituent of $R_{26}$ to $R_{29}$ are the same as those of the substituent of $R_{13}$ to $R_{18}$ in formula (1). $R_{26}$ to $R_{29}$ each is preferably a hydrogen atom, a halogen atom, a substituted carbonyl group having from 1 to 30 carbon atoms, an alkylamino group having from 1 to 30 carbon atoms, an arylamino group having from 6 to 30 carbon atoms, a sulfonylamino group having from 1 to 30 carbon atoms, an acylamino group having from 2 to 30 carbon atoms, a ureido group having from 1 to 30 carbon atoms, an alkoxycarbonylamino group having from 2 to 30 carbon atoms, an aryloxycarbonylamino group having from 7 to 30 carbon atoms, a carbamoylamino group having from 1 to 30 carbon atoms or a sulfamoylamino group having from 1 to 30 carbon atoms. Examples of the substituent of the substituted carbonyl group include an alkyl group, an aryl group, an alkoxy group, an aryloxy group, an arylamino group and an alkylamino group. $R_{26}$ to $R_{29}$ each is more preferably a hydrogen atom, an acylamino group having from 1 to 20 carbon atoms, a ureido group having from 1 to 20 carbon atoms, an alkoxycarbonylamino group having from 2 to 20 carbon atoms or an aryloxycarbonylamino group having from 7 to 20 carbon atoms. Still more preferably, either one of $R_{26}$ and $R_{29}$ is an acylamino group having from 1 to 20 carbon atoms, a ureido group having from 1 to 20 carbon atoms, an alkoxycarbonylamino group having from 2 to 20 carbon atoms or an aryloxycarbonylamino group having from 7 to 20 carbon atoms.

$R_{2a}$ represents a hydrogen atom, an alkyl group, an alkenyl group, an alkynyl group, an aryl group, a heterocyclic group, an unsubstituted amino group, an acylamino group, a sulfonylamino group, a carbamoylamino group, a sulfamoylamino group, an alkoxycarbonylamino group, an aryloxycarbonylamino group, a phosphoramido group, an acyl group, a carbamoyl group, a sulfonyl group, a sulfamoyl group, a cyano group or a halogen atom, preferably a hydrogen atom, a heterocyclic group, an unsubstituted amino group, an acylamino group, a sulfonylamino group, a carbamoylamino group, a sulfamoylamino group, an alkoxycarbonylamino group, an aryloxycarbonylamino group, an acyl group, a carbamoyl group, a sulfonyl group, a sulfamoyl group, a cyano group or a halogen atom, still more preferably a hydrogen atom, an acylamino group, a sulfonylamino group, a carbamoylamino group, a sulfamoylamino group, an alkoxycarbonylamino group, an aryloxycarbonylamino group, an acyl group, a carbamoyl group or a cyano group.

In formula (2), preferred is the combination such that $X_{21}$ is an oxygen atom or N—$R_{2b}$, $R_{2b}$ is a substituted or unsubstituted alkyl group having from 1 to 20 carbon atoms, a substituted carbonyl group having from 1 to 20 carbon atoms or a substituted sulfonyl group having from 0 to 20 carbon atoms, the substituent of the substituted carbonyl group is an aliphatic group, an aryl group, a heterocyclic group, an alkoxy group or an aryloxy group, the substituent of the substituted sulfonyl group is an aliphatic group or an aryl group, $Y_{21}$ is an oxygen atom, $R_{21}$ and $R_{22}$ each is an unsubstituted or substituted alkyl group having from 1 to 20 carbon atoms or an unsubstituted or substituted aryl group having from 6 to 20 carbon atoms and may combine with $R_{23}$ or $R_{24}$, respectively, to form a ring (preferably, a 5- or 6-membered alicyclic ring), for example, an indoline ring, a tetrahydroquinoline ring or a Julolidine ring, or $R_{21}$ and $R_{22}$ may be combined with each other to form a ring, for example, a pyrrolidine ring, a piperidine ring or a morpholine ring, $R_{23}$, $R_{24}$ and $R_{25}$ each is a hydrogen atom, a substituted or unsubstituted alkyl group having from 1 to 20 carbon atoms or a substituted or unsubstituted alkoxy group having from 1 to 20 carbon atoms, $R_{26}$ to $R_{29}$ each is a hydrogen atom, a sulfonylamino group having from 1 to 20 carbon atoms, an acylamino group having from 2 to 20 carbon atoms, a ureido group having from 1 to 20 carbon atoms, an alkoxycarbonylamino group having from 2 to 20 carbon atoms, an aryloxycarbonylamino group having from 7 to 20 carbon atoms, a carbamoylamino group having from 1 to 20 carbon atoms or a sulfamoylamino group having from 1 to 20 carbon atoms, and $R_{2a}$ is a hydrogen atom, a heterocyclic group having from 2 to 20 carbon atoms, an unsubstituted amino group, an acylamino group having from 2 to 20 carbon atoms, a sulfonylamino group having from 1 to 20 carbon toms, a carbamoylamino group having from 1 to 20 carbon atoms, a sulfamoylamino group having from 1 to 20 carbon atoms, an alkoxycarbonylamino group having from 2 to 20 carbon atoms, an aryloxycarbonylamino group having from 7 to 20 carbon atoms, an acyl group having from 2 to 20 carbon atoms, a carbamoyl group having from 1 to 20 carbon atoms, a sulfonyl group having from 1 to 20 carbon atoms, a sulfamoyl group having from 1 to 20 carbon atoms, a cyano group or a halogen atom, provided that when $X_{21}$ is an oxygen atom and $R_{2a}$ is a hydrogen atom, at least one of $R_{26}$ to $R_{29}$ is an unsubstituted or substituted amino group.

Formula (3) is described below.

$X_{31}$ represents an oxygen atom, a sulfur atom or N—$R_{3b}$, preferably an oxygen atom or N—$R_{3b}$. Examples and preferred range of $R_{3b}$ are the same as those of $R_{19}$ in formula (1). $Z_{31}$ represents $NR_{31}R_{32}$ or $OG_{31}$. Examples and preferred range of $R_{31}$ to $R_{35}$ are the same as those of $R_{11}$ to $R_{15}$ in formula (1).

$R_{36}$ represents a hydrogen atom or a substituent.

Examples of the substituent are set forth below, however, the present invention is by no means limited thereto:

- an alkyl group preferably having from 1 to 20 carbon atoms, more preferably from 1 to 12 carbon atoms, still more preferably from 1 to 8 carbon atoms, such as methyl, ethyl, iso-propyl, tert-butyl, n-octyl, n-decyl, n-hexadecyl, cyclopropyl, cyclopentyl and cyclohexyl;
- an alkenyl group preferably having from 2 to 20 carbon atoms, more preferably from 2 to 12 carbon atoms, still more preferably from 2 to 8 carbon atoms, such as vinyl, allyl, 2-butenyl and 3-pentenyl;
- an alkynyl group preferably having from 2 to 20 carbon atoms, more preferably from 2 to 12 carbon atoms, still more preferably from 2 to 8 carbon atoms, such as propargyl and 3-pentynyl;
- an aryl group preferably having from 6 to 30 carbon atoms, more preferably from 6 to 20 carbon atoms, still more preferably from 6 to 12 carbon atoms, such as phenyl, p-methylphenyl and naphthyl;
- a substituted carbonyl group preferably having from 1 to 20 carbon atoms, more preferably from 1 to 16 carbon atoms, still more preferably from 1 to 12 carbon atoms, such as acetyl, benzoyl, methoxycarbonyl, phenyloxycarbonyl, dimethylaminocarbonyl and phenylaminocarbonyl;
- a substituted amino group preferably having from 1 to 20 carbon atoms, more preferably from 1 to 16 carbon atoms, still more preferably from 1 to 12 carbon atoms, such as dimethylamino, methylcarbamoyl, ethylsulfonylamino, dimethylaminocarbonylamino and phthalimido;
- a sulfonyl group preferably having from 1 to 20 carbon atoms, more preferably from 1 to 16 carbon atoms, still more preferably from 1 to 12 carbon atoms, such as mesyl and tosyl;
- a heterocyclic group preferably having from 1 to 20 carbon atoms, more preferably from 1 to 16 carbon atoms, still more preferably from 1 to 12 carbon atoms (the hetero atom is, for example, oxygen, nitrogen or sulfur), such as imidazolyl, pyridyl, furyl, piperidyl, morpholino, benzoxazolyl and triazolyl;
- an alkoxy group preferably having from 1 to 20 carbon atoms, more preferably from 1 to 16 carbon atoms, still more preferably from 1 to 12 carbon atoms, such as methoxy and benzyloxy;
- an aryloxy group preferably having from 6 to 20 carbon atoms, more preferably from 6 to 16 carbon atoms, still more preferably from 6 to 12 carbon atoms, such as phenoxy and naphthyloxy;
- a halogen atom, preferably a fluorine atom, a chlorine atom, a bromine atom or an iodine atom;
- an alkylthio group preferably having from 1 to 20 carbon atoms, more preferably from 1 to 16 carbon atoms, still more preferably from 1 to 12 carbon atoms, such as methylthio;
- an arylthio group preferably having from 6 to 20 carbon atoms, more preferably from 6 to 16 carbon atoms, still more preferably from 6 to 12 carbon atoms, such as phenylthio; and additionally
- a sulfo group, a carboxyl group, a hydroxyl group, a thiol group and a cyano group.

These substituents each may further be substituted.

$R_{36}$ is preferably a cyano group, a substituted or unsubstituted aryl group, an aromatic heterocyclic group (for example, a substituted or unsubstituted benzazole group (e.g., benzoxazolyl) or a triazolyl group), a substituted carbonyl group (for example, a phenylaminocarbonyl group, a methoxycarbonyl group or t-butylcarbonyl group) or a substituted sulfonyl group (for example, a methanesulfonyl group). $R_{36}$ is more preferably a cyano group, a substituted or unsubstituted benzazole group (e.g., benzoxazolyl) or a substituted carbonyl group, still more preferably a substituted or unsubstituted benzazole group (e.g., benzoxazolyl) or a substituted carbonyl group.

$G_{31}$ represents a hydrogen atom, a substituent or a counter cation. Examples of the substituent include the substituents described above for $R_{3b}$. The counter cation is not particularly limited, however, examples thereof include a metal cation (e.g., lithium ion, sodium ion, aluminum ion, europium ion) and a quaternary ammonium ion (preferably having from 1 to 30 carbon atoms, more preferably from 1 to 20 carbon atoms, still more preferably from 1 to 10 carbon atoms, e.g., tetrabutylammonium ion). The metal cation may have a ligand.

$G_{31}$ is preferably a hydrogen atom, a substituted or unsubstituted alkyl group (preferably having from 1 to 30 carbon atoms, more preferably from 1 to 20 carbon atoms, still more preferably from 1 to 10 carbon atoms, e.g., methyl, isopropyl, methoxyethoxymethyl), a substituted or unsubstituted aryl group (preferably having from 6 to 30 carbon atoms, more preferably from 6 to 20 carbon atoms, still more preferably from 6 to 10 carbon atoms, e.g., phenyl, p-methoxyphenyl), an alkali metal ion, an alkaline earth metal ion, an aluminum ion, a zinc ion, a europium ion, a borate ion or a quaternary ammonium ion.

$G_{31}$ is more preferably a hydrogen atom, a substituted or unsubstituted alkyl group, an alkali metal ion or a quaternary ammonium ion, still more preferably a hydrogen atom or a substituted or unsubstituted alkyl group.

Formula (4) is described-below.

The compound represented by formula (4) is included in the compound represented by formula (2).

The compound of formula (4) is preferably represented by the following formula (5), (6), (7), (8) or (9):

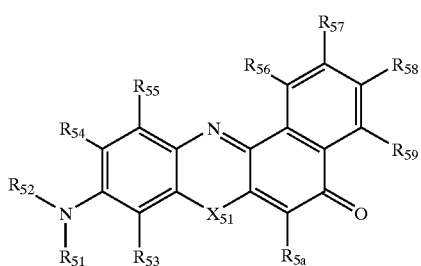

(5)

In formula (5), preferred is the combination such that $X_{51}$ is an oxygen atom, a sulfur atom or N—$R_{5b}$, $R_{5b}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{51}$ and $R_{52}$ each is an unsubstituted or substituted alkyl group having from 1 to 20 carbon atoms or an unsubstituted or substituted aryl group having from 6 to 20 carbon atoms and may combine with $R_{53}$ or $R_{54}$, respectively, to form a ring (preferably a 5- or 6-membered alicyclic ring), for example, an indoline ring, a tetrahydroquinoline ring or a Julolidine ring, or $R_{51}$ and $R_{52}$ may be combined with each other to form a ring, for example, a pyrrolidine ring, a piperidine ring or a morpholine ring, $R_{53}$, $R_{54}$ and $R_{55}$ each is a hydrogen atom, a substituted or unsubstituted alkyl group having from 1 to 20 carbon atoms, a halogen atom, a hydroxy group, a substituted or unsubstituted alkoxy group having from 1 to 20 carbon atoms or an unsubstituted amino group or a substituted amino group having from 1 to 20 carbon atoms, $R_{56}$ to $R_{59}$ each is a hydrogen tom, a halogen atom, a substituted carbonyl group having from 1 to 30 carbon atoms, an alkylamino group having from 1 to 30 carbon atoms, an arylamino group having from 6 to 30 carbon atoms, a sulfonylamino group having from 1 to 30 carbon atoms, an acylamino group having from 2 to 30 carbon atoms, a ureido group having from 1 to 30 carbon atoms, an alkoxycarbonylamino group having from 2 to 30 carbon atoms, an aryloxycarbonylamino group having from 7 to 30 carbon atoms, a carbamoylamino group having from 1 to 30 carbon atoms or a sulfamoylamino group having from 0 to 30 carbon atoms, provided that at least one of $R_{56}$ to $R_{59}$ is an unsubstituted or substituted amino group, and $R_{5a}$ is a hydrogen atom or a cyano group.

More preferred is the combination such that $X_{51}$ is an oxygen atom or N—$R_{5b}$, $R_{5b}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{51}$ and $R_{52}$ each is an unsubstituted or substituted alkyl group having from 1 to 20 carbon atoms or an unsubstituted or substituted aryl group having from 6 to 20 carbon atoms and may combine with $R_{53}$ or $R_{54}$, respectively, to form a ring (preferably a 5- or 6-memered alicyclic ring), for example, an indole ring, a quinoline ring or a Julolidine ring, or $R_{51}$ and $R_{52}$ may be combined with each other to form a ring, for example, a pyrrolidine ring, a piperidine ring or a morpholine ring, $R_{53}$, $R_{54}$ and $R_{55}$ each is a hydrogen atom, a substituted or unsubstituted alkyl group having from 1 to 20 carbon atoms or a substituted or unsubstituted alkoxy group having from 1 to 20 carbon atoms, $R_{56}$ to $R_{59}$ each is a hydrogen atom, a sulfonylamino group having from 1 to 20 carbon atoms, an acylamino group having from 2 to 20 carbon atoms, a ureido group having from 1 to 20 carbon atoms, an alkoxycarbonylamino group having from 2 to 20 carbon atoms, an aryloxycarbonylamino group having from 7 to 20 carbon atoms, a carbamoylamino group having from 1 to 20 carbon atoms or a sulfamoylamino group having from 1 to 20 carbon atoms, provided that at least one of $R_{56}$ to $R_{59}$ is an acylamino group having from 2 to 20 carbon atoms, a sulfonylamino group having from 1 to 20 carbon atoms, a ureido group having from 1 to 20 carbon atoms, an alkoxycarbonylamino group having from 2 to 20 carbon atoms, an aryloxycarbonylamino group having from 7 to 20 carbon atoms, a carbamoylamino group having from 1 to 20 carbon atoms or a sulfamoylamino group having from 0 to 20 carbon atoms, and $R_{5a}$ is a hydrogen atom or a cyano group.

Still more preferred is the combination such that $X_{51}$ is an oxygen atom or N—$R_{5b}$, $R_{5b}$ is a substituted or unsubstituted alkyl group having from 1 to 20 carbon atoms, $R_{51}$ and $R_{52}$ each is a substituted or unsubstituted alkyl group having from 1 to 12 carbon atoms or an unsubstituted or substituted aryl group having from 6 to 12 carbon atoms and may combine with $R_{53}$ or $R_{54}$, respectively, to form a ring or $R_{51}$ and $R_{52}$ may be combined with each other to form a ring, $R_{53}$, $R_{54}$ and $R_{55}$ each is a hydrogen atom, a substituted or unsubstituted alkyl group having from 1 to 12 carbon atoms or a substituted or unsubstituted alkoxy group having from 1 to 12 carbon atoms, $R_{56}$ to $R_{59}$ each is a hydrogen atom, a sulfonylamino group having from 1 to 12 carbon atoms, an acylamino group having from 2 to 12 carbon atoms, a ureido group having from 1 to 12 carbon atoms, an alkoxycarbonylamino group having from 2 to 12 carbon atoms, an aryloxycarbonylamino group having from 7 to 12 carbon atoms, preferably, either one of $R_{56}$ and $R_{59}$ is a sulfonamido group having from 1 to 12 carbon atoms, a carbonamido group having from 2 to 12 carbon atoms, a ureido group having from 1 to 12 carbon atoms, an alkoxycarbonylamino group having from 2 to 12 carbon atoms or an aryloxycarbonylamino group having from 7 to 12 carbon atoms and the others each is a hydrogen atom, and $R_{5a}$ is a hydrogen atom or a cyano group.

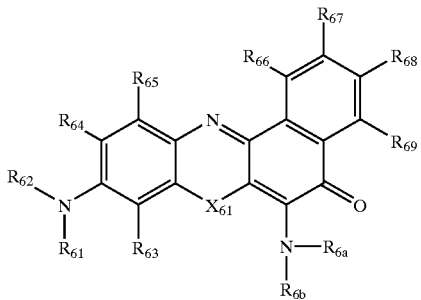

(6)

In formula (6), preferred is the combination such that $X_{61}$ is an oxygen atom or N—$R_{6c}$, $R_{6c}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{61}$ and $R_{62}$ each is an unsubstituted or substituted alkyl group having from 1 to 20 carbon atoms or an unsubstituted or substituted aryl group having from 6 to 20 carbon atoms and may combine with $R_{63}$ or $R_{64}$, respectively, to form a ring (preferably, a 5- or 6-membered alicyclic ring), for example, an indoline ring, a tetrahydroquinoline ring or a Julolidine ring or $R_{61}$ and $R_{62}$ may be combined with each other to form a ring, for example, a pyrrolidine ring, a piperidine ring or a morpholine ring, $R_{63}$, $R_{64}$ and $R_{65}$ each is a hydrogen atom, a substituted or unsubstituted alkyl group having from 1 to 20 carbon atoms, a halogen atom, a hydroxy group, a substituted or unsubstituted alkoxy group having from 1 to 20 carbon atoms, an unsubstituted amino group or a substituted amino group having from 1 to 20 carbon atoms, $R_{66}$ to $R_{69}$ each is a hydrogen atom, a halogen atom, a substituted carbonyl group having from 1 to 30 carbon atoms, an alkylamino group having from 1 to 30 carbon atoms, an arylamino group having from 1 to 30 carbon atoms, a sulfonylamino group having from 1 to 30 carbon atoms, an acylamino group having from 2 to 30 carbon atoms, a ureido group having from 1 to 30 carbon atoms, an alkoxycarbonylamino group having from 2 to 30 carbon atoms, an aryloxycarbonylamino group having from 7 to 30 carbon atoms, a carbamoylamino group having from 1 to 30 carbon atoms or a sulfamoylamino group having from 0 to 30 carbon atoms, and $R_{6a}$ and $R_{6b}$ each is a hydrogen atom, an alkyl group, an alkenyl group, an alkynyl group, an aryl group, a heterocyclic group, an acyl group, an alkoxycarbonyl group, an aryloxycarbonyl group, a heterocyclic oxycarbonyl group, a sulfonyl group, a carbamoyl group or a sulfamoyl group, provided that $R_{6a}$ or $R_{6b}$ is not combined with any one of $R_{61}$ to $R_{69}$ to form a ring.

More preferred is the combination such that $X_{61}$ is an oxygen atom or N—$R_{6c}$, $R_{6c}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{61}$ and $R_{62}$ each is an unsubstituted or substituted alkyl group having from 1 to 20 carbon atoms or an unsubstituted or substituted aryl group having from 6 to 20 carbon atoms and may combine with $R_{63}$ or $R_{64}$, respectively, to form a ring (preferably, a 5- or 6-membered alicyclic ring), for example, an indoline ring, a tetrahydroquinoline ring or a Julolidine ring or $R_{61}$ and $R_{62}$ may be combined with each other to form a ring, for example, a pyrrolidine ring, a piperidine ring or a morpholine ring, $R_{63}$, $R_{64}$ and $R_{65}$ each is a hydrogen atom, a substituted or unsubstituted alkyl group having from 1 to 20 carbon atoms or a substituted or unsubstituted alkoxy group having from 1 to 20 carbon atoms, $R_{66}$ to $R_{69}$ each is a hydrogen atom, a sulfonylamino group having from 1 to 20 carbon atoms, an acylamino group having from 2 to 20 carbon atoms, a ureido group having from 1 to 20 carbon atoms, an alkoxycarbonylamino group having from 2 to 20 carbon atoms, an aryloxycarbonylamino group having from 7 to 20 carbon atoms, a carbamoylamino group having from 1 to 20 carbon atoms or a sulfamoylamino group having from 0 to 20 carbon atoms, and $R_{6a}$ and $R_{6b}$ each is a hydrogen atom, an acyl group having from 1 to 20 carbon atoms, a sulfonyl group having from 1 to 20 carbon atoms, a carbamoyl group having from 1 to 20 carbon atoms, a Sulfamoyl group having from 0 to 20 carbon atoms or an alkoxycarbonyl group having from 2 to 20 carbon atoms, provided that $R_{6a}$ or $R_{6b}$ is not combined with any one of $R_{61}$ to $R_{69}$ to form a ring.

Still more preferred is the combination such that $X_{61}$ is an oxygen atom or N—$R_{6c}$, $R_{6c}$ is a substituted or unsubstituted alkyl group having from 1 to 20 carbon atoms, $R_{61}$ and $R_{62}$ each is a substituted or unsubstituted alkyl group having from 1 to 12 carbon atoms or an unsubstituted or substituted aryl group having from 6 to 12 carbon atoms and may combine with $R_{63}$ or $R_{64}$, respectively, to form a ring or $R_{61}$ and $R_2$ may be combined with each other to form a ring, $R_{63}$, $R_{64}$ and $R_{65}$ each is a hydrogen atom, a substituted or unsubstituted alkyl group having from 1 to 12 carbon atoms or a substituted or unsubstituted alkoxy group having from 1 to 12 carbon atoms, $R_{66}$ to $R_{69}$ each is a hydrogen atom, a sulfonylamino group having from 1 to 12 carbon atoms, an acylamino group having from 2 to 12 carbon atoms, a ureido group having from 1 to 12 carbon atoms, an alkoxycarbonylamino group having from 2 to 12 carbon atoms or an aryloxycarbonylamino group having from 7 to 12 carbon atoms, and $R_{6a}$ and $R_{6b}$ each is a hydrogen atom, an acyl group having from 1 to 12 carbon atoms, a sulfonyl group having from 1 to 12 carbon atoms, a carbamoyl group having from 1 to 12 carbon atoms, a sulfamoyl group having from 0 to 12 carbon atoms or an alkoxycarbonyl group having from 2 to 12 carbon atoms, provided that $R_{6a}$ or $R_{6b}$ is not combined with any one of $R_{61}$ to $R_{69}$ to form a ring.

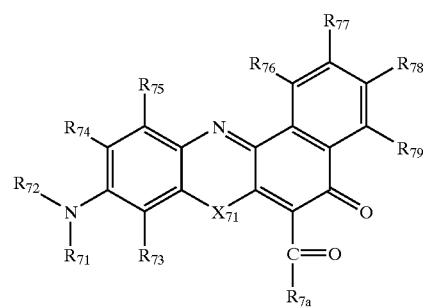

(7)

In formula (7), preferred is the combination such that $X_{71}$ is an oxygen atom or N—$R_{7b}$, $R_{7b}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{71}$ and $R_{72}$ each is an unsubstituted or substituted alkyl group having from 1 to 20 carbon atoms or an unsubstituted or substituted aryl group having from 6 to 20 carbon atoms and may combine with $R_{73}$ or $R_{74}$, respectively, to form a ring (preferably, a 5- or 6-membered alicyclic ring), for example, an indoline ring, a tetrahydroquinoline ring or a Julolidine ring or $R_{71}$ and $R_{72}$ may be combined with each other to form a ring, for example, a pyrrolidine ring, a piperidine ring or a morpholine ring, $R_{73}$, $R_{74}$ and $R_{75}$ each is a hydrogen atom, a substituted or unsubstituted alkyl group having from 1 to 20 carbon atoms, a halogen atom, a hydroxy group, a substituted or unsubstituted alkoxy group having from 1 to 20 carbon atoms, an unsubstituted amino group or a substituted amino group having from 1 to 20 carbon atoms, $R_{76}$ to $R_{79}$ each is a hydrogen atom, a halogen atom, a substituted carbonyl group having from 1 to 30 carbon atoms, an alkylamino group having from 1 to 30 carbon atoms, an arylamino group having from 6 to 30 carbon atoms, a sulfonylamino group having from 1 to 30 carbon atoms, an acylamino group having from 2 to 30 carbon atoms, a ureido group having from 1 to 30 carbon atoms, an alkoxycarbonylamino group having from 2 to 30 carbon atoms, an aryloxycarbonylamino group having from 7 to 30 carbon atoms, a carbamoylamino group having from 1 to 30 carbon atoms or a sulfamoylamino group having from 0 to 30 carbon atoms, and $R_{7a}$ is an aryl group, an alkoxy group, an aryloxy group, a heterocyclic oxy group, an unsubstituted or substituted amino group or a hydroxy group.

More preferred is the combination such that $X_{71}$ is an oxygen atom or N—$R_{7b}$, $R_{7b}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{71}$ and $R_{72}$ each is an unsubstituted or substituted alkyl group having from 1 to 20 carbon atoms or an unsubstituted or substituted aryl group having from 6 to 20 carbon atoms and may combine with $R_{73}$ or $R_{74}$, respectively, to form a ring (preferably, a 5- or 6-membered alicyclic ring), for example, an indoline ring, a tetrahydroquinoline ring or a Julolidine ring or $R_{71}$ and $R_{72}$ may be combined with each other to form a ring, for example, a pyrrolidine ring, a piperidine ring or a morpholine ring, $R_{73}$, $R_{74}$ and $R_{75}$ each is a hydrogen atom, a substituted or unsubstituted alkyl group having from 1 to 20 carbon atoms or a substituted or unsubstituted alkoxy group having from 1 to 20 carbon atoms, $R_{76}$ to $R_{79}$ each is a hydrogen atom, a sulfonylamino group having from 1 to 20 carbon atoms, an acylamino group having from 2 to 20 carbon atoms, a ureido group having from 1 to 20 carbon atoms, an alkoxycarbonylamino group having from 2 to 20 carbon atoms, an aryloxycarbonylamino group having from 7 to 20 carbon atoms, a carbamoylamino group having from 1 to 20 carbon atoms or a sulfamoylamino group having from 0 to 20 carbon atoms, and $R_{7a}$ is an aryl group having from 6 to 20 carbon atoms, an unsubstituted amino group or a substituted amino group having from 1 to 20 carbon atoms.

Still more preferred is the combination such that $X_{71}$ is an oxygen atom or N—$R_{7b}$, $R_{7b}$ is a substituted or unsubstituted alkyl group having from 1 to 20 carbon atoms, $R_{71}$ and $R_{72}$ each is a substituted or unsubstituted alkyl group having from 1 to 12 carbon atoms or an unsubstituted or substituted aryl group having from 6 to 12 carbon atoms and may combine with $R_{73}$ or $R_{74}$, respectively, to form a ring or $R_{71}$ and $R_{72}$ may be combined with each other to form a ring, $R_{73}$, $R_{74}$ and $R_{75}$ each is a hydrogen atom, a substituted or unsubstituted alkyl group having from 1 to 12 carbon atoms or a substituted or unsubstituted alkoxy group having from 1 to 12 carbon atoms, $R_{76}$ to $R_{79}$ each is a hydrogen atom, a sulfonylamino group having from 1 to 12 carbon atoms, an acylamino group having from 2 to 12 carbon atoms, a ureido group having from 1 to 12 carbon atoms, an alkoxycarbonylamino group having from 2 to 12 carbon atoms or an aryloxycarbonylamino group having from 7 to 12 carbon atoms, and $R_{7a}$ is a substituted or unsubstituted amino group having from 1 to 12 carbon atoms, particularly preferably a substituted amino group in which the substituent is an alkyl group having from 1 to 12 carbon atoms or an aryl group having from 6 to 12 carbon atoms.

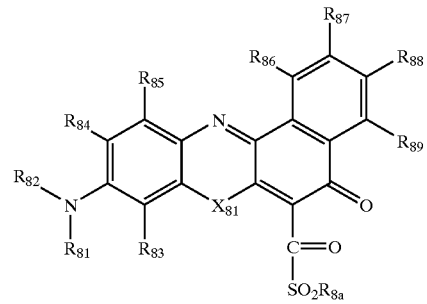

(8)

In formula (8), preferred is the combination such that $X_{81}$ is an oxygen atom, a sulfur atom or N—$R_{8b}$, $R_{8b}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{81}$ and $R_{82}$ each is an unsubstituted or substituted alkyl group having from 1 to 20 carbon atoms or an unsubstituted or substituted aryl group having from 6 to 20 carbon atoms and may combine with $R_{83}$ or $R_{84}$, respectively, to form a ring (preferably, a 5- or 6-membered alicyclic ring), for example, an indoline ring, a tetrahydroquinoline ring or a Julolidine ring or $R_{81}$ and $R_{82}$ may be combined with each other to form a ring, for example, a pyrrolidine ring, a piperidine ring or a morpholine ring, $R_{83}$, $R_{84}$ and $R_{85}$ each is a hydrogen atom, a substituted or unsubstituted alkyl group having from 1 to 20 carbon atoms, a halogen atom, a hydroxy group, a substituted or unsubstituted alkoxy group having from 1 to 20 carbon atoms, an unsubstituted amino group or a substituted amino group having from 1 to 20 carbon atoms, $R_{86}$ to $R_{89}$ each is a hydrogen atom, a halogen atom, a substituted carbonyl group having from 1 to 30 carbon atoms, an alkylamino group having from 1 to 30 carbon atoms, an arylamino group having from 6 to 30 carbon atoms, a sulfonylamino group having from 1 to 30 carbon atoms, an acylamino group having from 2 to 30 carbon atoms, a ureido group having from 1 to 30 carbon atoms, an alkoxycarbonylamino group having from 2 to 30 carbon atoms, an aryloxycarbonylamino group having from 7 to 30 carbon atoms, a carbamoylamino group having from 1 to 30 carbon atoms or a sulfamoylamino group having from 0 to 30 carbon atoms, and $R_{8a}$ is an aliphatic group, an aryl group, an alkoxy group, a substituted or unsubstituted amino group or a hydroxy group.

More preferred is the combination such that $X_{81}$ is an oxygen atom or N—$R_{8b}$, $R_{8b}$ is a hydrogen atom, a substituted or unsubstituted alkyl group having from 1 to 20 carbon atoms, a substituted carbonyl group having from 1 to 20 carbon atoms or a substituted sulfonyl group having from 0 to 20 carbon atoms, $R_{81}$ and $R_{82}$ each is an unsubstituted or substituted alkyl group having from 1 to 20 carbon atoms or an unsubstituted or substituted aryl group having from 6 to 20 carbon atoms and may combine with $R_{83}$ or $R_{84}$, respectively, to form a ring (preferably, a 5- or 6 membered alicyclic ring), for example, an indoline ring, a tetrahydroquinoline ring or a Julolidine ring or $R_{81}$ and $R_{82}$ may be combined with each other to form a ring, for example, a pyrrolidine ring, a piperidine ring or a morpholine ring, $R_{83}$, $R_{84}$ and $R_{85}$ each is a hydrogen atom, a substituted or unsubstituted alkyl group having from 1 to 20 carbon atoms or a substituted or unsubstituted alkoxy group having from 1 to 20 carbon atoms, $R_{86}$ to $R_{89}$ each is a hydrogen atom, a sulfonylamino group having from 1 to 20 carbon atoms, an acylamino group having from 2 to 20 carbon atoms, a ureido group having from 1 to 20 carbon atoms, an alkoxycarbonylamino group having from 2 to 20 carbon atoms, an aryloxycarbonylamino group having from 7 to 20 carbon atoms, a carbamoylamino group having from 1 to 20 carbon atoms or a sulfamoylamino group having from 0 to 20 carbon atoms, and $R_{8a}$ is an alkyl group having from 1 to 20 carbon atoms, an alkenyl group, an alkynyl group, an aryl group having from 6 to 20 carbon atoms, an alkoxy group having from 1 to 20 carbon atoms, an unsubstituted amino group or a substituted amino group having from 1 to 20 carbon atoms.

Still more preferred is the combination such that $X_{81}$ is an oxygen atom or N—$R_{8b}$, $R_{8b}$ is a substituted or unsubstituted alkyl group having from 1 to 20 carbon atoms, $R_{81}$ and $R_{82}$ each is a substituted or unsubstituted alkyl group having from 1 to 12 carbon atoms or an unsubstituted or substituted aryl group having from 6 to 12 carbon atoms and may combine with $R_{83}$ or $R_{84}$, respectively, to form a ring or $R_{81}$ and $R_{82}$ may be combined with each other to form a ring, $R_{83}$, $R_{84}$ and $R_{85}$ each is a hydrogen atom, a substituted or unsubstituted alkyl group having from 1 to 12 carbon atoms or a substituted or unsubstituted alkoxy group having from 1 to 12 carbon atoms, $R_{86}$ to $R_{89}$ each is a hydrogen atom, a sulfonylamino group having from 1 to 12 carbon atoms, an acylamino group having from 2 to 12 carbon atoms, a ureido group having from 1 to 12 carbon atoms, an alkoxycarbonylamino group having from 2 to 12 carbon atoms or an aryloxycarbonylamino group having from 7 to 12 carbon atoms, and $R_{8a}$ is an alkyl group having from 1 to 12 carbon atoms, an alkenyl group, an alkynyl group, an aryl group having from 6 to 12 carbon atoms, a substituted or unsubstituted amino group having from 1 to 12 carbon atoms, particularly preferably a substituted amino group having from 1 to 12 carbon atoms in which the substituent is an alkyl group having from 1 to 12 carbon atoms or an aryl group having from 6 to 12 carbon atoms.

The compounds represented by formulae (1) to (4) each may be a low molecular weight compound. A high molecular weight compound (preferably having a weight-average molecular weight of from 1,000 to 5,000,000, more preferably from 5,000 to 2,000,000, still more preferably from 10,000 to 1,000,000) where a residue represented by formula (1), (2), (3) or (4) is connected to the polymer main chain or a high molecular weight compound (preferably having a weight-average molecular weight of from 1,000 to 5,000,000, more preferably from 5,000 to 2,000,000, still more preferably from 10,000 to 1,000,000) having a skeleton of formula (1), (2), (3) or (4) in the main chain may also be used. In the case of a high molecular weight compound, the compound may be either a homopolymer or a copolymer with another monomer.

The compounds represented by formulae (1) to (4) each is preferably a low molecular weight compound. For the sake of convenience, formulae (1) to (4) each is shown as a limiting structure but tautomers thereof may also be used.

Examples of the compounds represented by formulae (1) to (4) are set forth below, however, the present invention is by no means limited thereto.

Examples of the Compound of Formula (1):

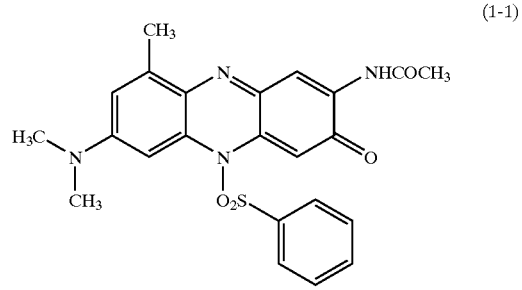
(1-1)

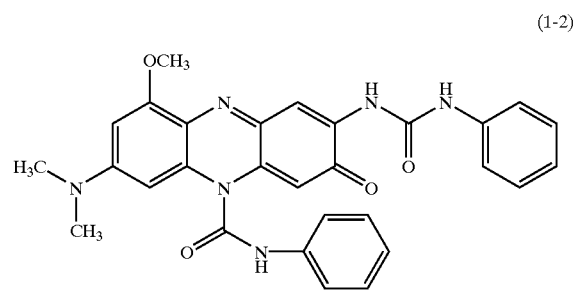
(1-2)

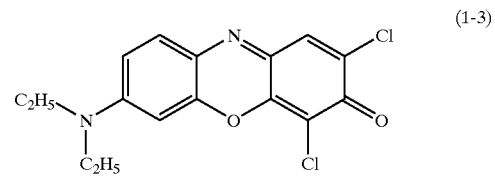
(1-3)

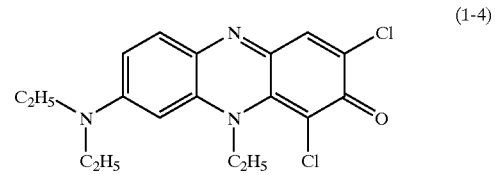
(1-4)

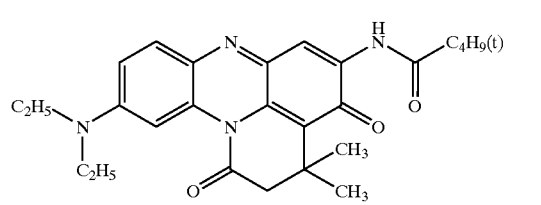
(1-5)

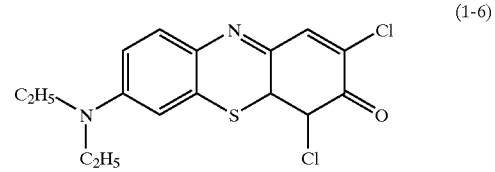
(1-6)

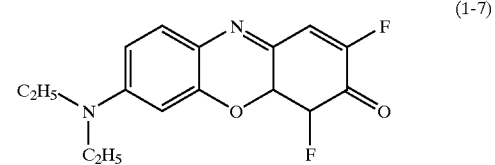
(1-7)

Examples of the Compounds of Formulae (2) and (4):
2-1
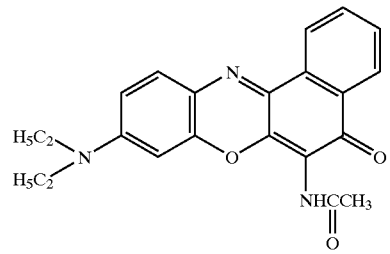
2-2
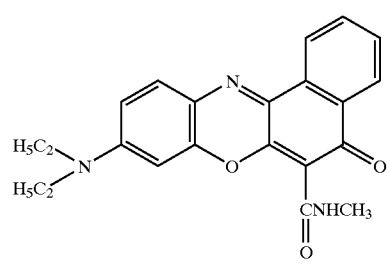
2-3
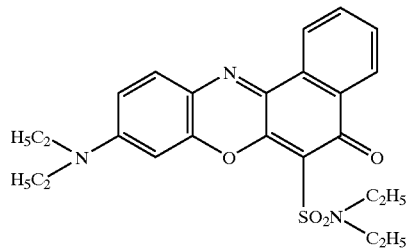
2-4
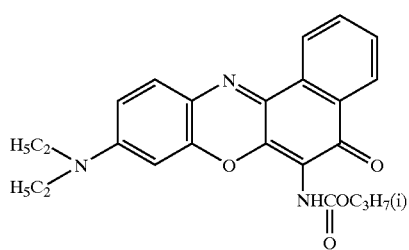
2-5
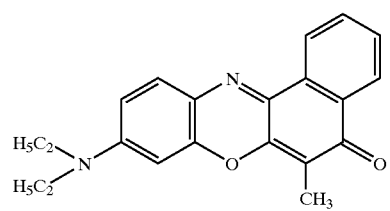
2-6
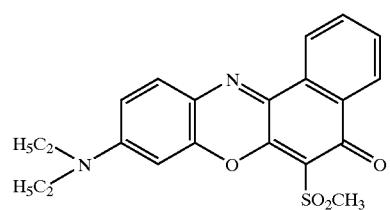
2-7
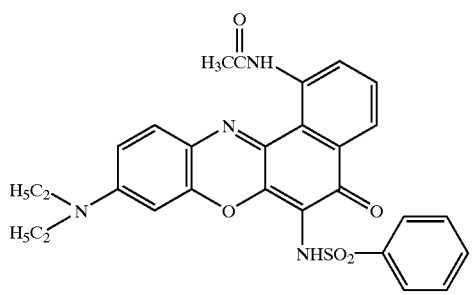
2-8
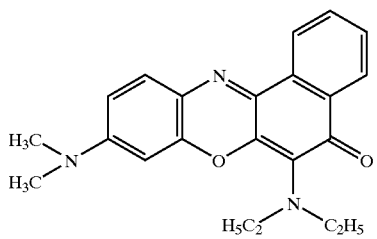
2-9
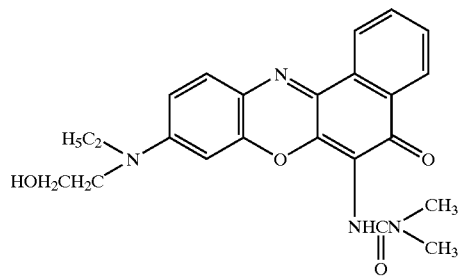
2-10
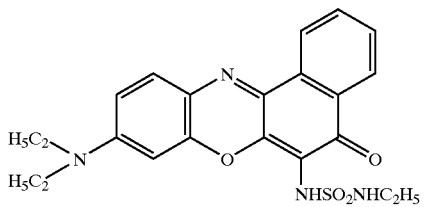
2-11
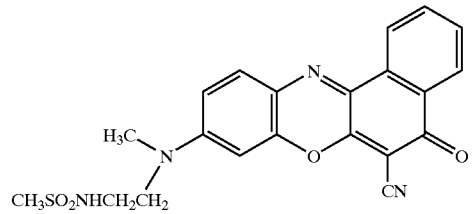
2-12
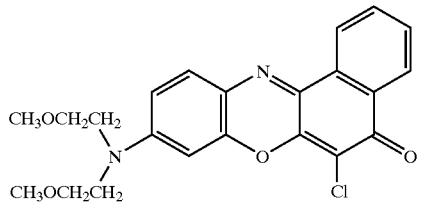

-continued
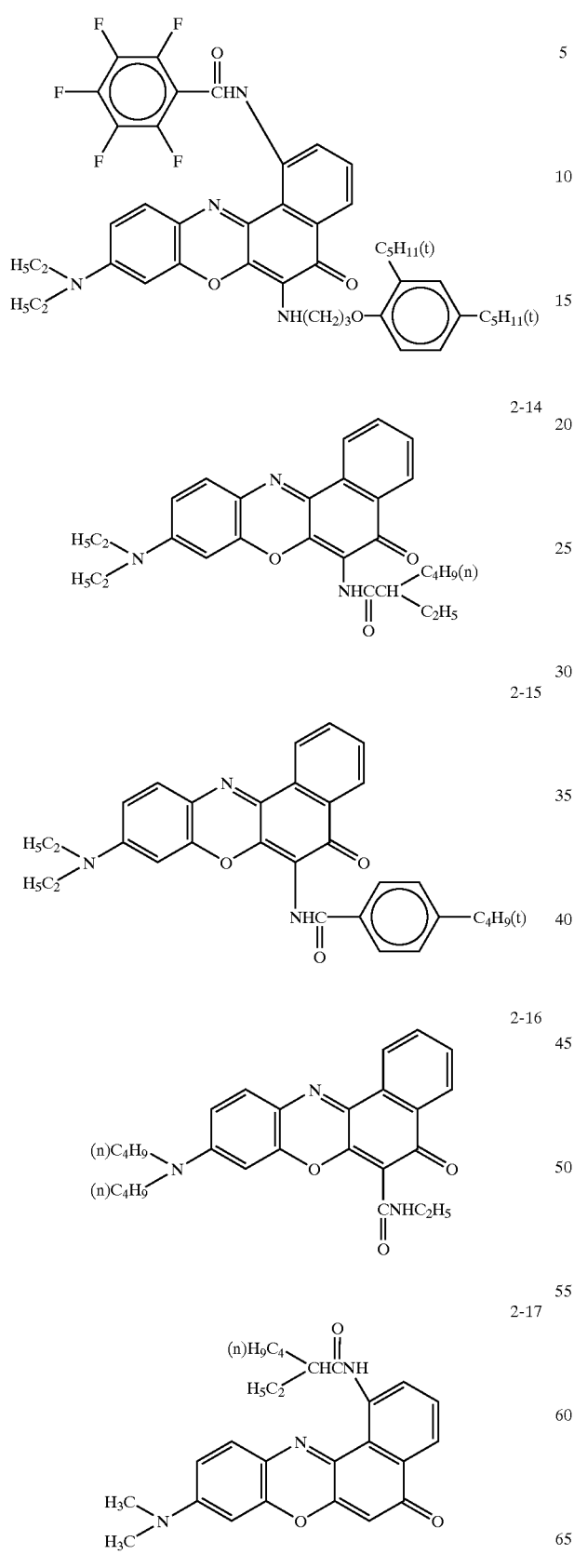
2-13
2-14
2-15
2-16
2-17
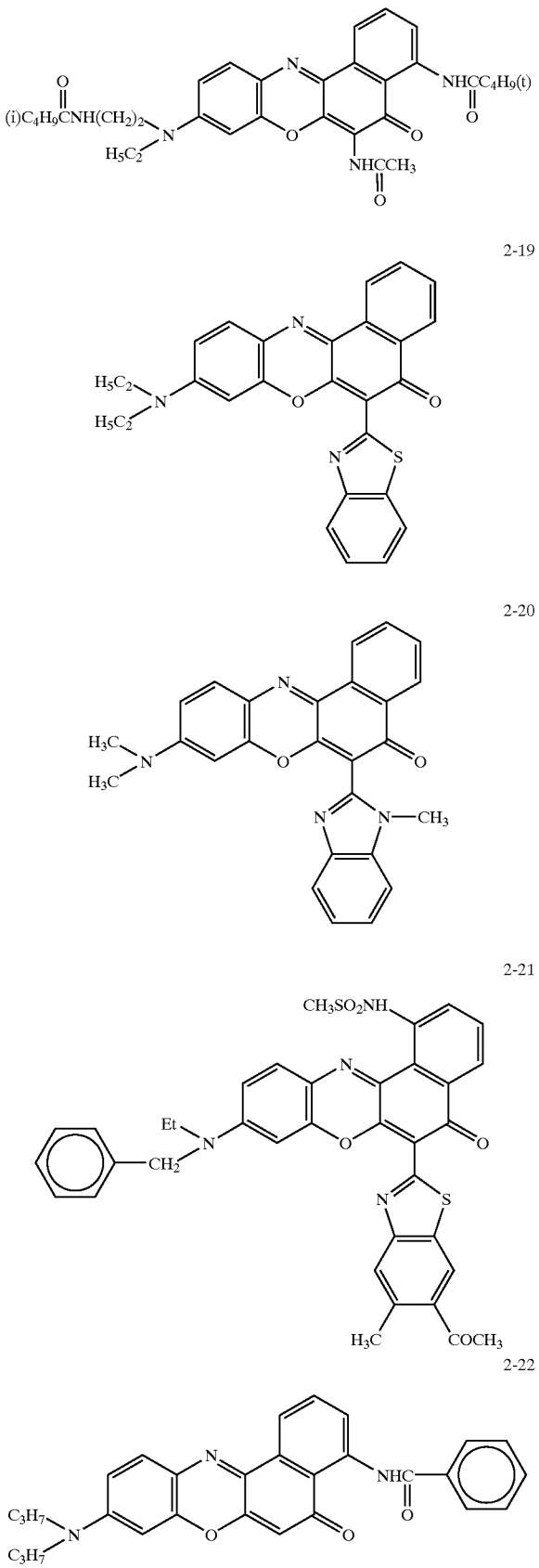
2-18
2-19
2-20
2-21
2-22

-continued
2-23
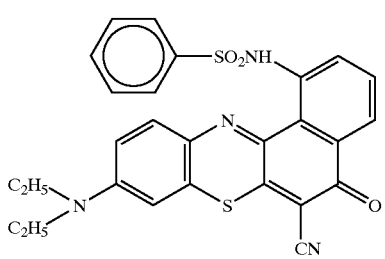
2-24
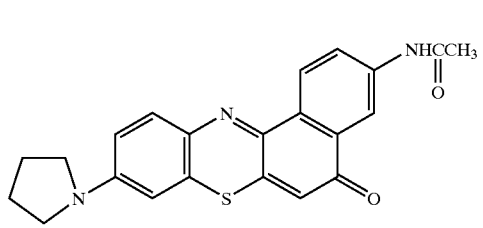
2-25
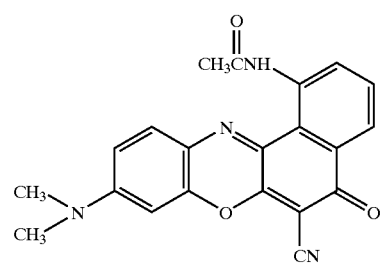
2-26
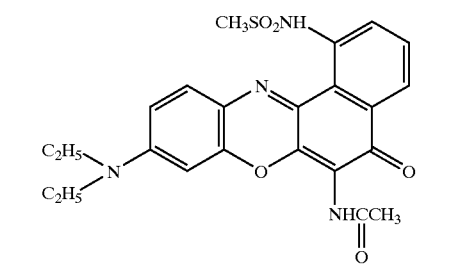
2-27
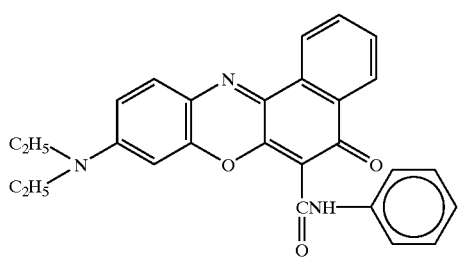
2-28
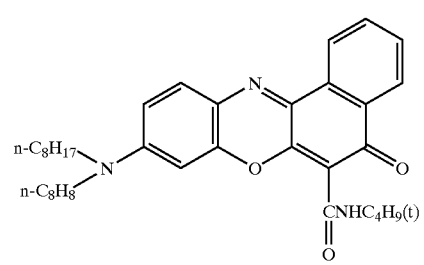
-continued
2-29
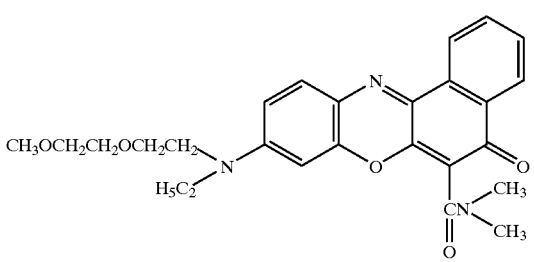
2-30
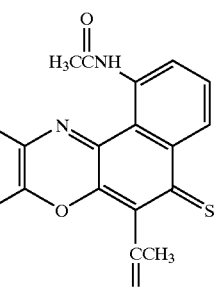
2-31
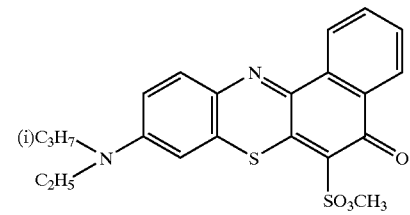
2-32
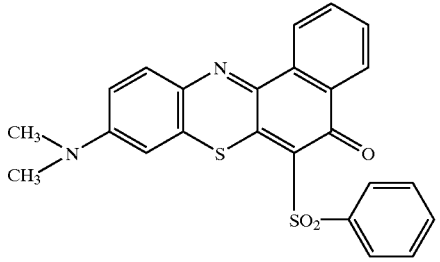
2-33
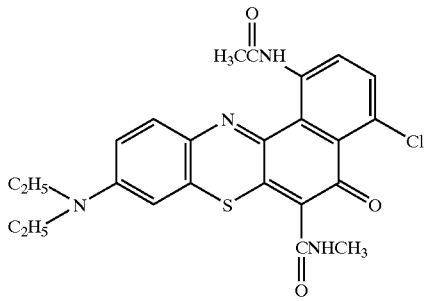
2-34
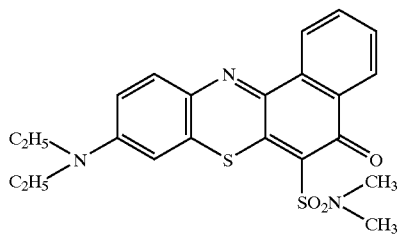

2-35 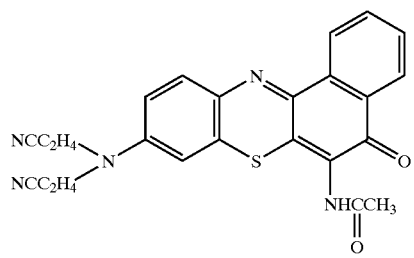
2-41 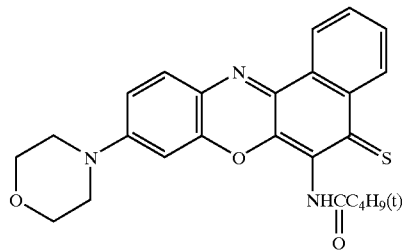
2-36 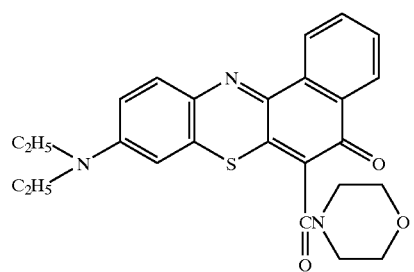
2-42 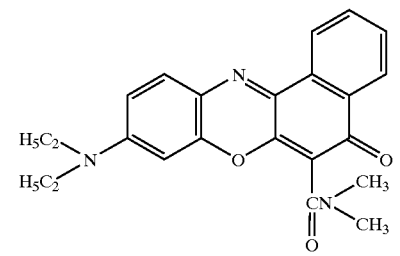
2-37 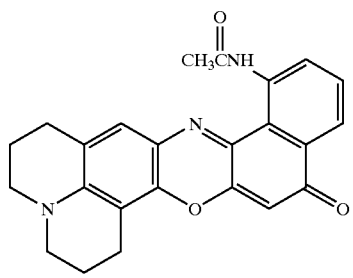
2-43 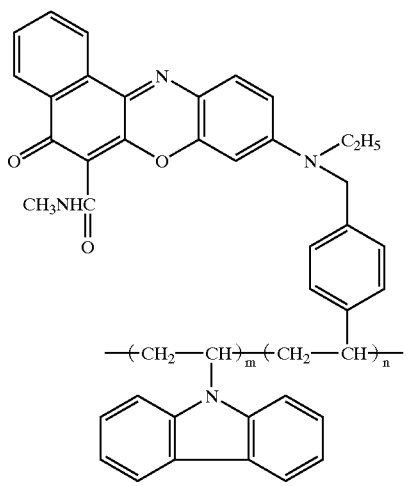
2-38 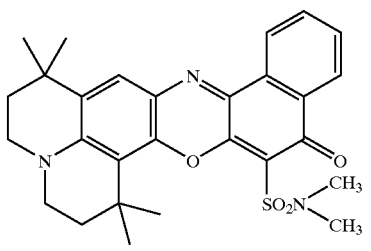
2-39 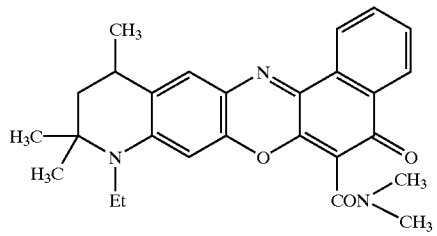
2-44 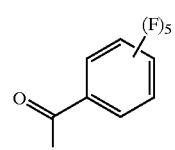
2-40 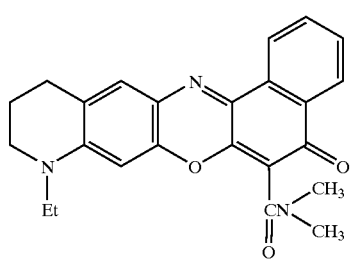
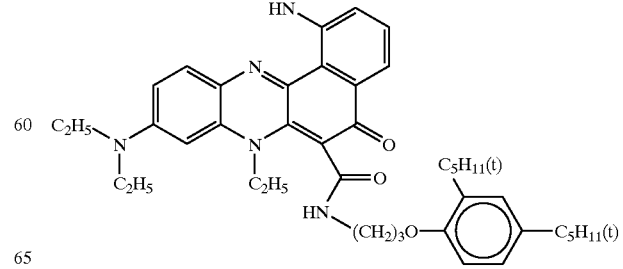

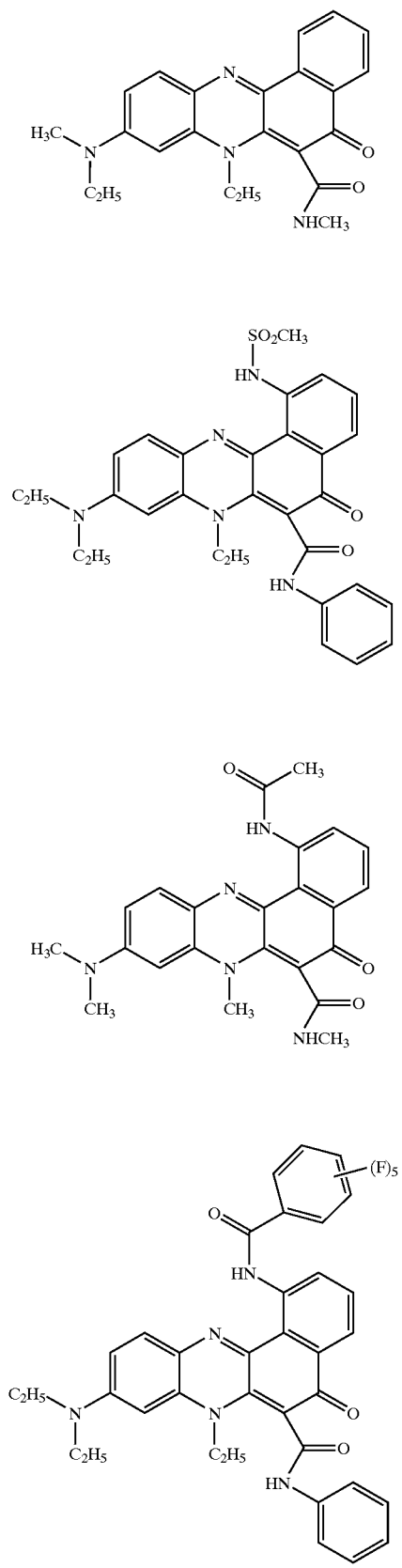
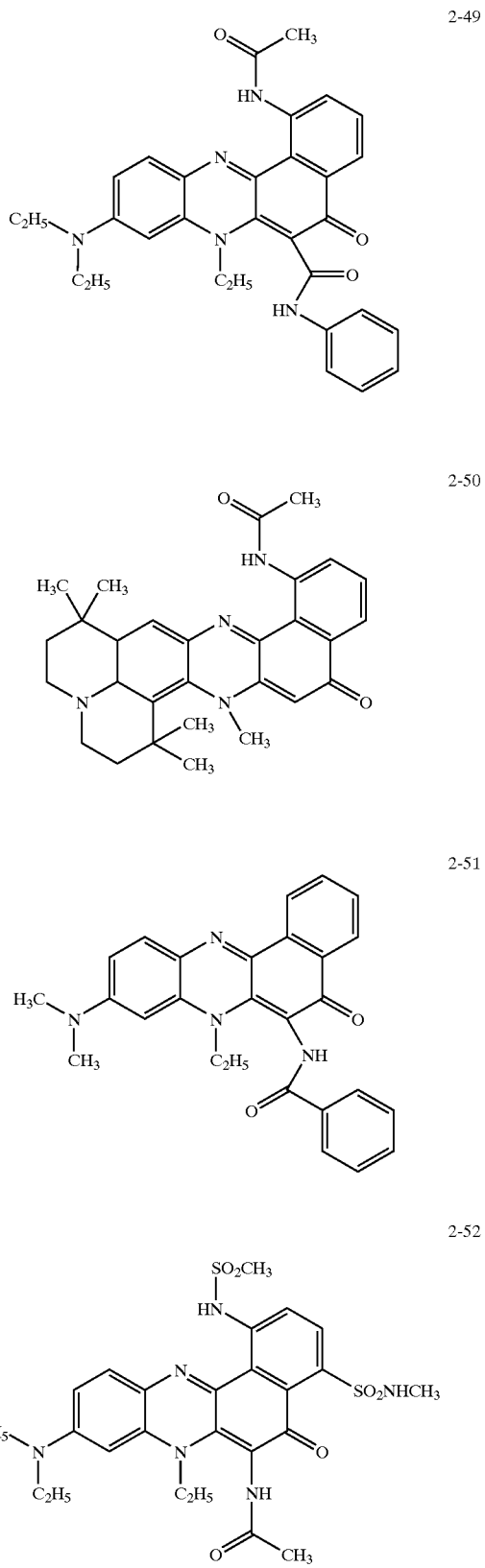

-continued
2-53
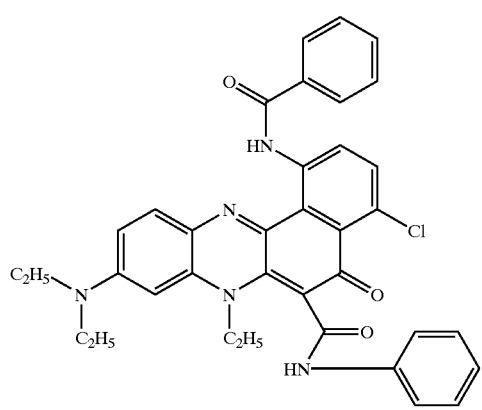
2-54
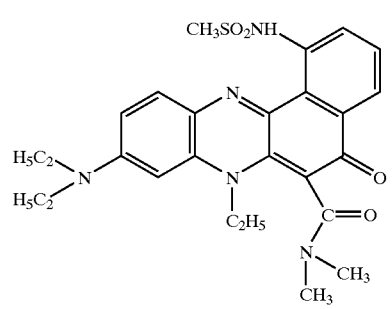
2-55
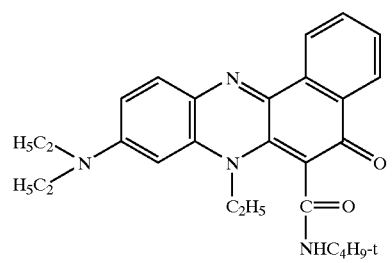
2-56
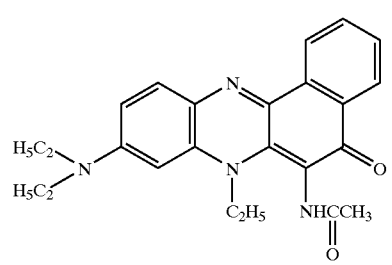
2-57
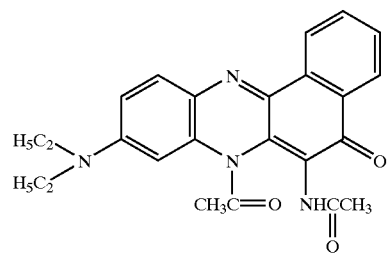
-continued
2-58
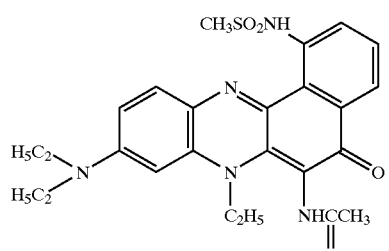
2-59
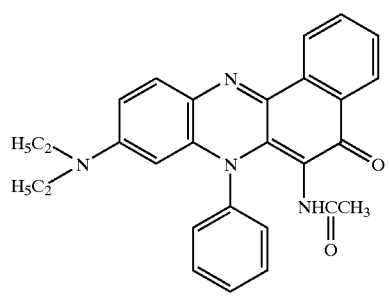
2-60
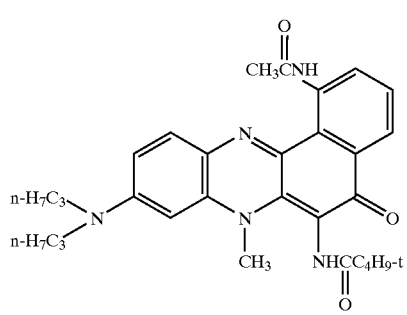
2-61
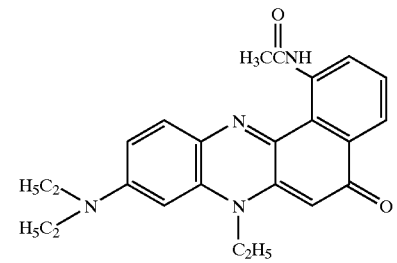
2-62
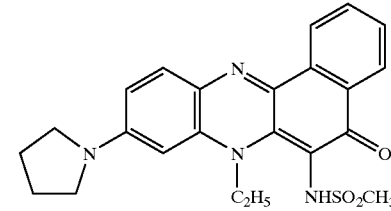
2-63
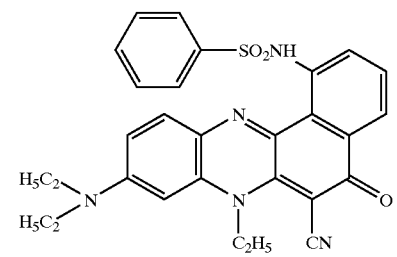

2-64
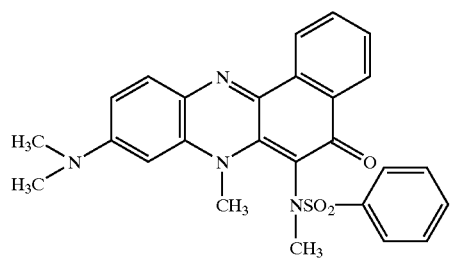
2-65
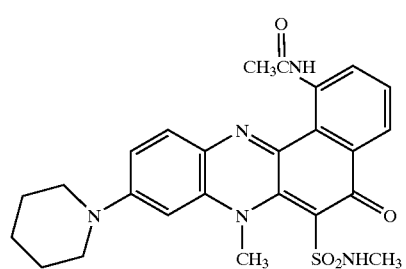
2-66
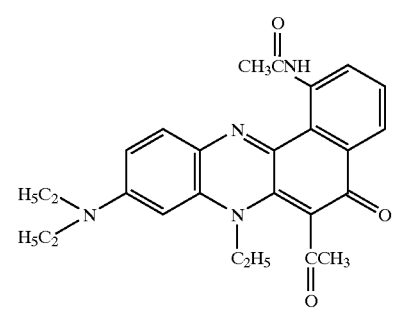
2-67
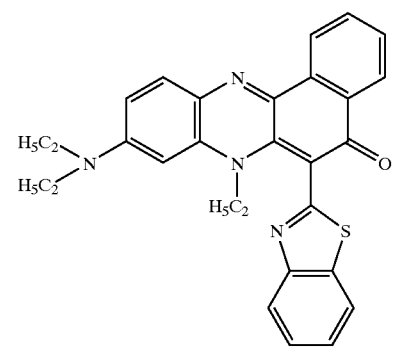
2-68
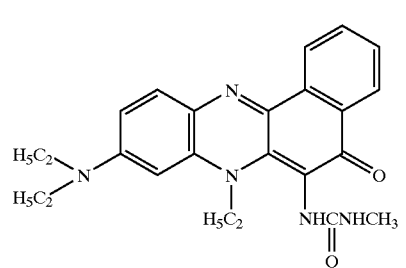
2-69
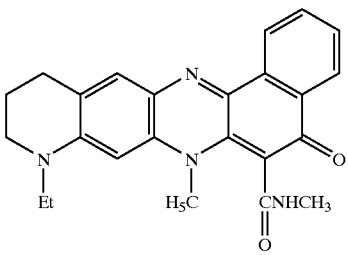
2-70
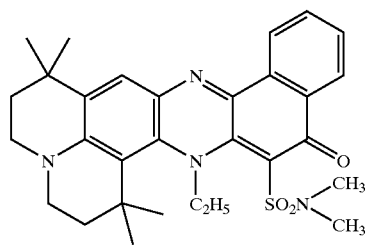
2-71
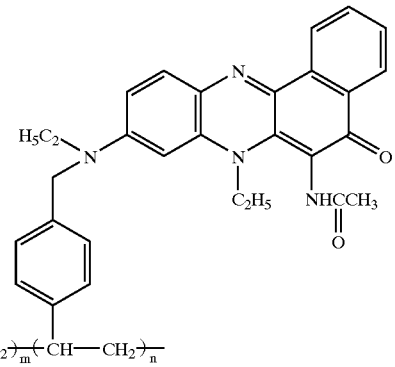
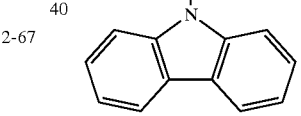
2-72
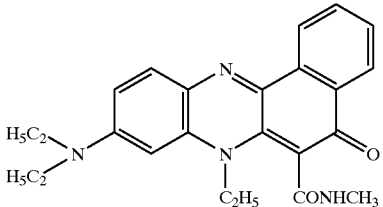
2-73
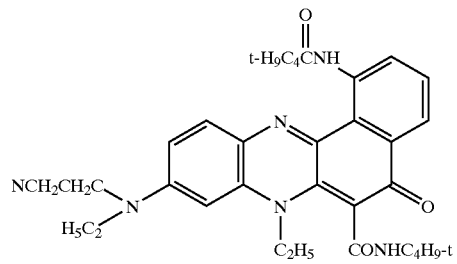

Examples of the Compound of Formula (3):
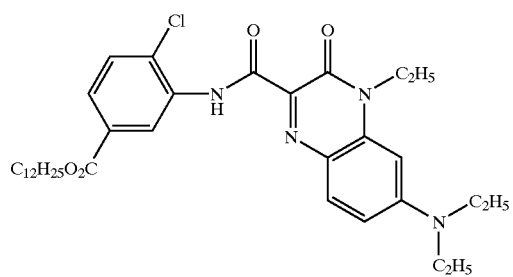 3-1
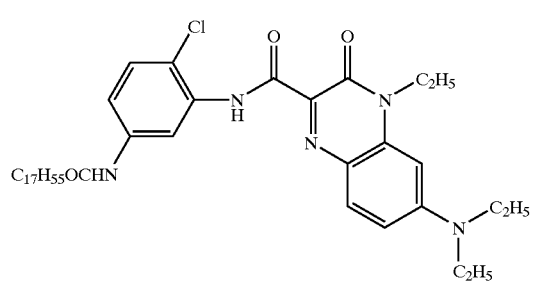 3-2
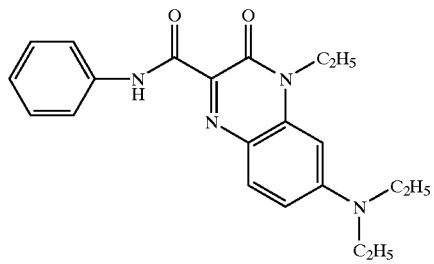 3-3
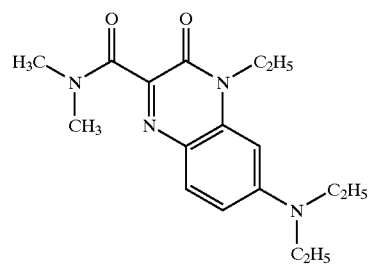 3-4
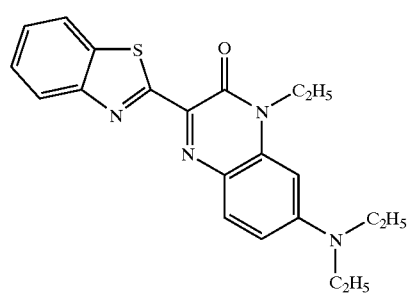 3-5
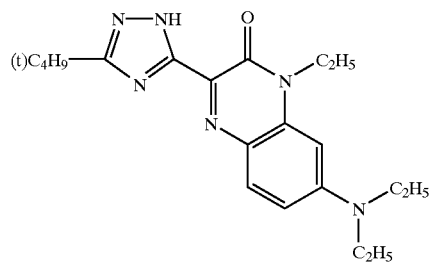 3-6
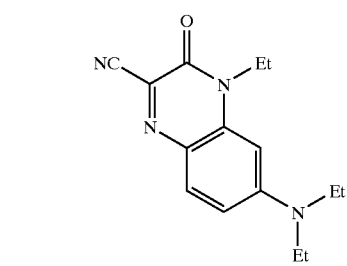 3-7
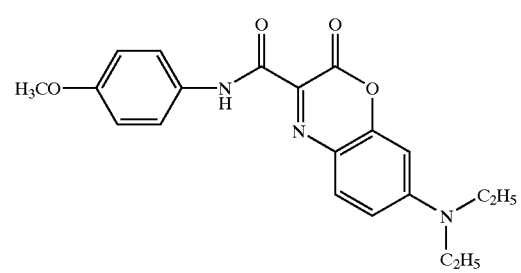 3-8
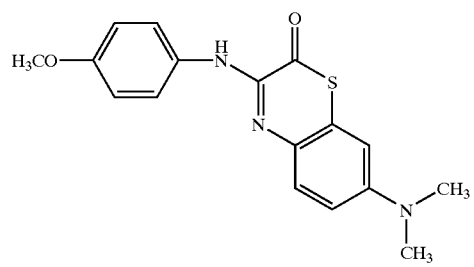 3-9
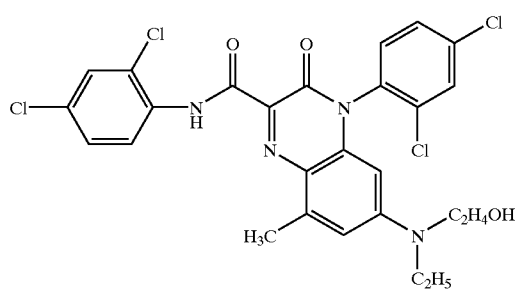 3-10

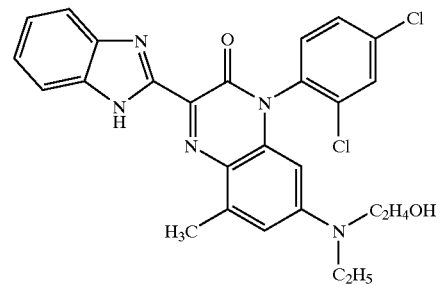

3-11

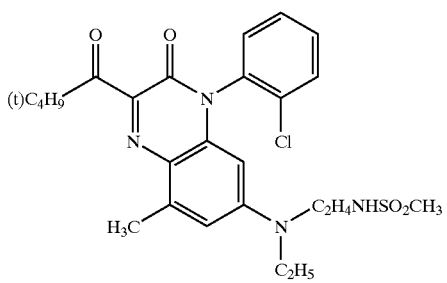

3-12

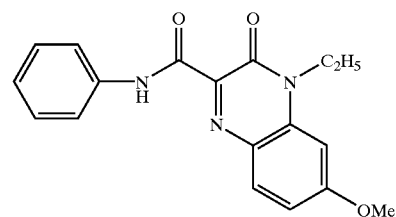

3-13

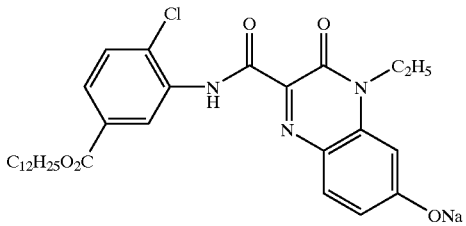

3-14

The synthesis method of the compounds of the present invention is described below. The compounds of the present invention can be synthesized by various methods, however, in general, the compounds are synthesized by a method of reacting an o-nitrosophenol with a naphthol derivative to cause cyclization and thereby synthesize the compound or a method of oxidation coupling phenylenediamine or an aminophenol with phenol, naphthol or aniline described in items ([5] to [7] above as shown in the following Synthesis Examples.

Some synthesis examples of the compounds of the present invention are described below.

SYNTHESIS EXAMPLE 1

Synthesis of Compound (1-3)

Compound (1-3) was synthesized by the method shown below.

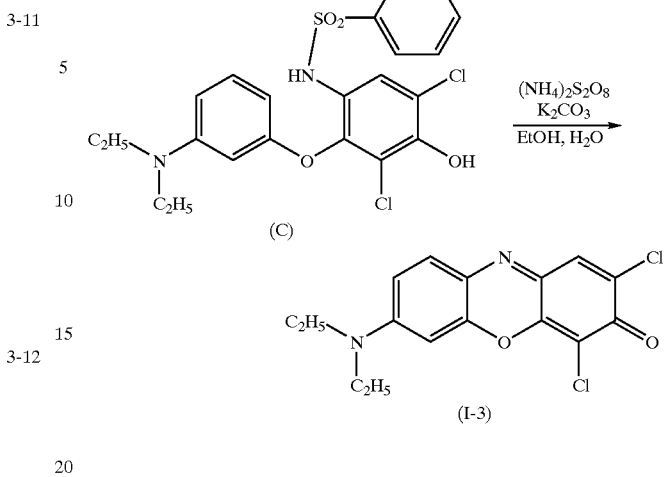

More specifically, 5 ml of ethanol and 1 ml of water were added to 0.5 g of a phenol derivative (c) and the mixture was stirred at room temperature. Thereto, 0.5 g of potassium carbonate and 0.5 g of ammonium persulfate were added and the mixture was stirred at room temperature for one hour. After the completion of reaction, ethyl acetate and water was added to the reaction solution and the organic layer separated was washed with water. The residue was crystallized in an ethyl acetate/hexane system to obtain 0.17 g of crystals of Compound (1-3). The absorption spectrum determined in ethyl acetate revealed that λmax was 596 nm.

SYNTHESIS EXAMPLE 2

Synthesis of Compound (2-2):

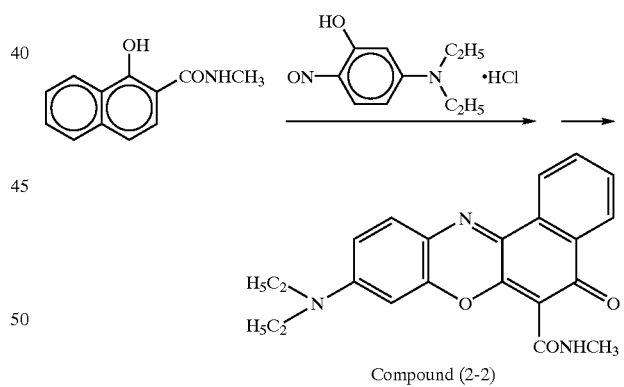

A solution obtained by dissolving 6.03 g of 2-methylcarbamoyl-1-naphthol and 2-nitroso-5-diethylamino-phenol hydrochloride into 50 ml of dimethylformamide was stirred under heating at 110° C. for 5 hours. After the completion of reaction, the temperature of the reaction solution was lowered to room temperature, water was poured into the solution, crystals precipitated was collected by filtration, washed with water and dried, and the crude crystals obtained were purified through a column and then crystallized from chloroform-ethyl acetate. As a result, 1.38 g of Compound (2-2) was obtained (absorption spectrum λmax: 570 nm ($ClCH_2CH_2Cl$)).

SYNTHESIS EXAMPLE 3

Synthesis of Compound (2-26)

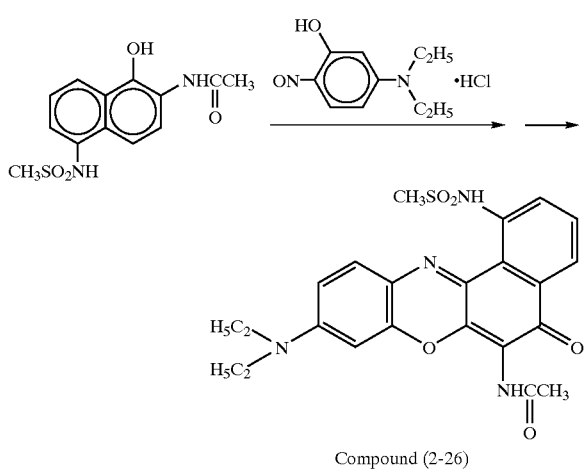

Compound (2-26)

In the same manner as in Synthesis Example 1, 611 mg of Compound (2-26) was obtained (absorption spectrum λmax: 576 nm).

SYNTHESIS EXAMPLE 4

In the same manner as in Synthesis Example 1, Compound (2-1) was obtained (absorption spectrum λmax: 552 nm).

SYNTHESIS EXAMPLE 5

In the same manner as in Synthesis Example 1, Compound (2-27) was obtained (absorption spectrum λmax: 582 nm).

SYNTHESIS EXAMPLE 6

In the same manner as in Synthesis Example 1, Compound (2-28) was obtained (absorption spectrum λmax: 562 nm).

SYNTHESIS EXAMPLE 7

In the same manner as in Synthesis Example 1, Compound (2-42) was obtained (absorption spectrum λmax: 551 nm).

SYNTHESIS EXAMPLE 8

Synthesis of Compound (2-44):

Compound (2-44) was synthesized by the method shown below.

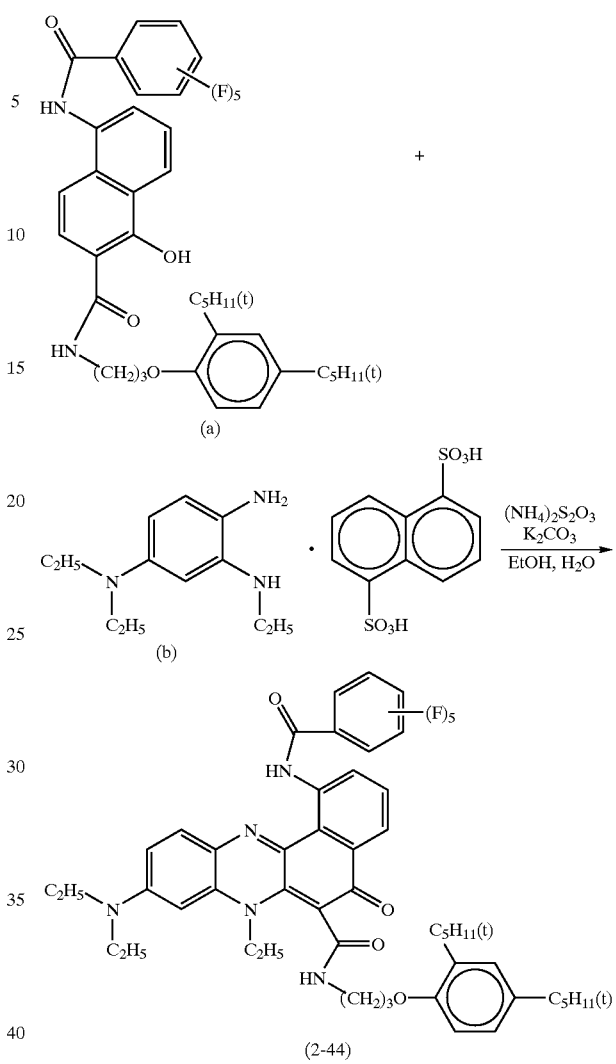

(2-44)

More specifically, to 1.1 g of an amine derivative (b) and 1.0 g of a phenol derivative (a), 5 ml of ethanol and 1 ml of water were added and the mixture was stirred at room temperature. Thereto, 1.05 g of potassium carbonate and 1.0 g of ammonium persulfate were added and the mixture was stirred at room temperature for one hour. After the completion of reaction, ethyl acetate and water were added to the reaction solution and the organic layer separated was washed with 1N aqueous hydrochloric acid. The organic layer was dried over sodium sulfate and concentrated to obtain crude crystals of Compound (2-44). The crude crystals were purified by the column chromatography (hexane/ethyl acetate system) to obtain 0.4 g of crystals of Compound (2-44). The absorption spectrum of Compound (2–44) determined in ethyl acetate revealed that λmax was 548 nm and e was 57,000.

SYNTHESIS EXAMPLE 9

Synthesis of Compound (2-56):

According to the synthesis scheme shown below, 2.9 g of Compound (2-56) was synthesized in the same manner as in Synthesis Example of Compound (2-44). The absorption spectrum determined in dichloroethane revealed that λmax was 524 nm.

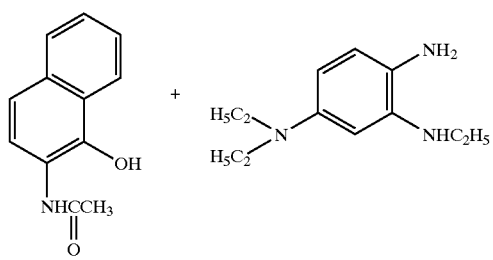

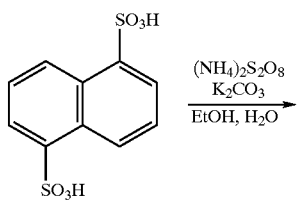

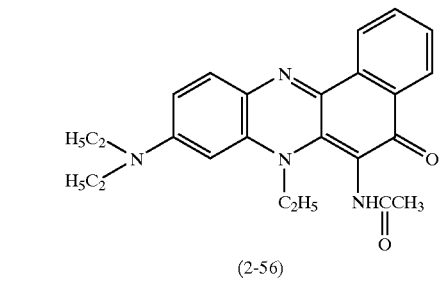

(2-56)

SYNTHESIS EXAMPLE 10

Synthesis of Compound (2-58):

According to the synthesis scheme shown below, 0.5 g of Compound (2-58) was synthesized in the same manner as in Synthesis Example of Compound (2-44). The absorption spectrum determined in dichloroethane revealed that λmax was 555 nm.

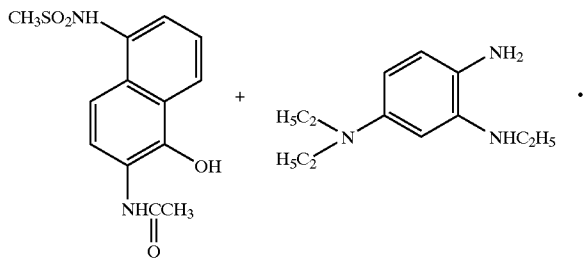

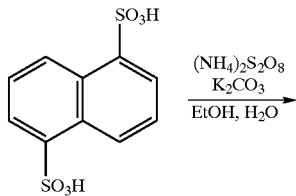

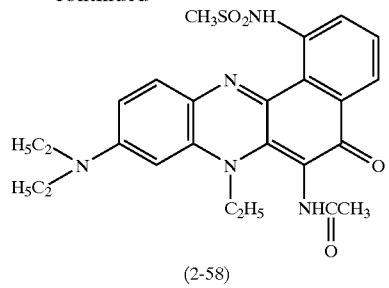

(2-58)

SYNTHESIS EXAMPLE 11

Synthesis of Compound (2-55)):

According to the synthesis scheme shown below, 3.1 g of Compound (2-55) was synthesized in the same manner as in Synthesis Example of Compound (2-44). The absorption spectrum determined in dichloroethane revealed that λmax was 548 nm.

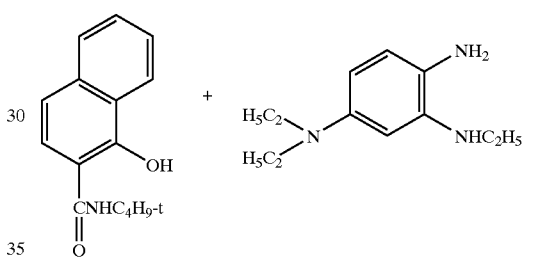

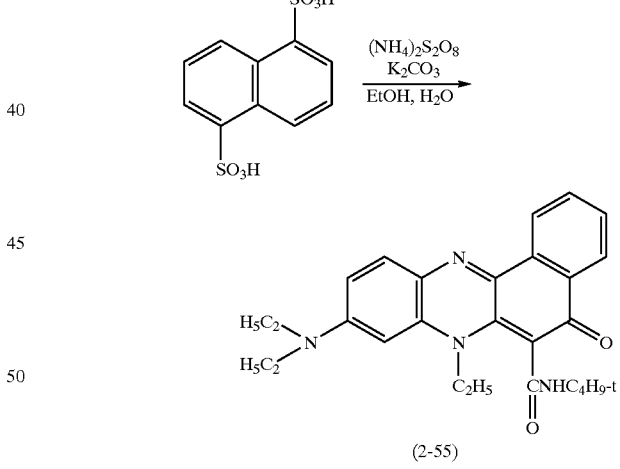

(2-55)

SYNTHESIS EXAMPLE 12

Synthesis of Compound (2-72):

According to the synthesis scheme shown below, 2.7 g of Compound (2-72) was synthesized in the same manner as in Synthesis Example of Compound (2-44). The absorption spectrum determined in dichloroethane revealed that λmax was 546 nm.

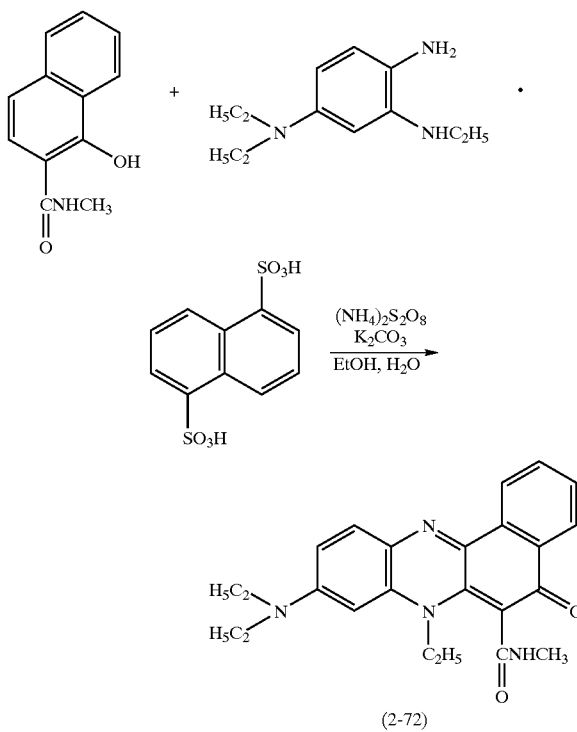

(2-72)

SYNTHESIS EXAMPLE 13

Synthesis of Compound (3-1):

According to the synthesis scheme shown below, Compound (3-1) was synthesized.

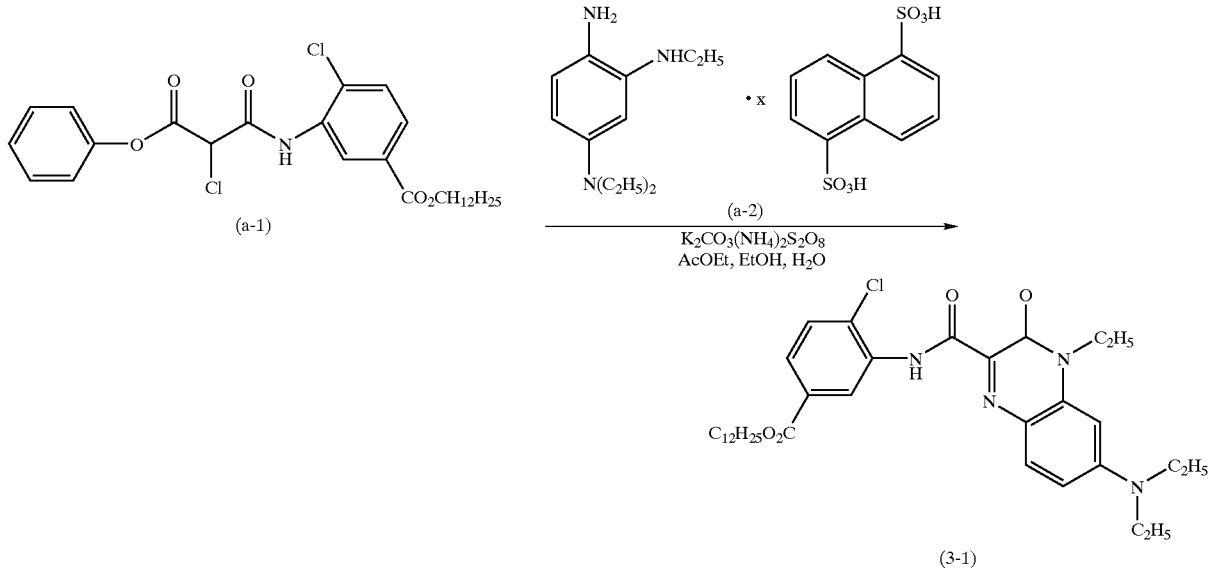

1 g of a phenyl ester (a-1) and 0.88 g of a phenylenediamine derivative (a-2) were dissolved in a mixed solvent comprising 8 ml of ethyl acetate, 2 ml of ethanol and 10 ml of water and thereto, 0.82 g of potassium carbonate and 0.8 g of ammonium persulfate were added, followed by stirring at room temperature for 30 minutes. The reaction solution was diluted with 30 ml of ethyl acetate and 10 ml of water and the organic layer separated was washed with aqueous hydrochloric acid and then with water. The organic layer was dried over sodium sulfate and the organic solution was concentrated to obtain crude crystals. The crude crystals obtained were purified by the column chromatography (hexane/ethyl acetate system) to obtain 0.6 g of a cyclic azine dye (3-1). This dye had optical characteristics shown below.

λmax=442 (nm) (in ethyl acetate), ε=29900.

The EL device containing a cyclic azine-type dye of the present invention is described below. The method for forming an organic layer of an EL device containing a cyclic azine-type dye of the present invention is not particularly limited, however, a resistance heating evaporation method, an electron beam method, a sputtering method, a molecular lamination method and a coating method may be used and in view of properties and production, a resistance heating evaporation method and a coating method are preferred.

The electroluminescence device of the present invention is a device comprising a pair of electrodes of an anode and a cathode having formed therebetween a light emitting layer or a plurality of organic compound thin films including a light emitting layer. In addition to the light emitting layer, a hole injecting layer, a hole transporting layer, an electron injecting layer, an electron transporting layer and a protective layer may also be provided. These layers each may have another function. For forming respective layers, various materials can be used.

The anode feeds holes to the hole injecting layer, the hole transporting layer or the light emitting layer and may use a metal, an alloy, a metal oxide, an electrically conductive compound or a mixture thereof but preferably uses a material having a work function of 4 eV or more. Specific examples thereof include an electrically conductive metal oxide such as tin oxide, zinc oxide, indium oxide and indium tin oxide (ITO), a metal such as gold, silver, chromium and nickel, a mixture or laminate of the metal with the electrically conductive metal oxide, an inorganic electrically conductive material such as copper iodide and copper sulfide, an organic electrically conductive material such as polyaniline, polythiophene and polypyrrole, and a laminate of the material with ITO. Of these, an electrically conductive metal oxide is preferred and in view of productivity, high electrical conductivity and transparency, ITO is more preferred. The thickness of the anode may be freely decided depending on the material used, however, it is usually in the range of preferably from 10 nm to 5 µm, more preferably from 50 nm to 1 tm, still more preferably from 100 to 500 nm.

The anode is usually used as a layer formed on a soda lime glass, an alkali-free glass or a transparent resin substrate. In the case of using a glass, the constructive material therefor is preferably an alkali-free glass so as to reduce the ion dissolved out from the glass. In the case of using a soda lime glass, the glass is preferably subjected to barrier coating with silica or the like. The thickness of the substrate is not particularly limited as far as the substrate can maintain the mechanical strength, however, in the case of using a glass, it is usually 0.2 mm or more, preferably 0.7 mm or more.

The anode may be prepared by various methods according to the material used and for example, in the case of ITO, the film is formed by an electron beam method, a sputtering method, a resistance heating evaporation method, a chemical reaction method (sol-gel process) or a method of coating an indium tin oxide dispersion.

By subjecting the anode to rinsing or other processings, the device driving voltage can be reduced or light emission efficiency can be increased. For example, in the case of ITO, UV-ozone treatment and plasma treatment are effective.

The cathode feeds electrons to the electron injecting layer, the electron transporting layer or the light emitting layer and is selected by taking account of the adhesion to the layer adjacent to the negative electrode, such as an electron injecting layer, an electron transporting layer and a light emitting layer, the ionization potential and the stability. As the material for the cathode, a metal, an alloy, a metal halide, a metal oxide, an electrically conductive compound or a mixture thereof may be used and specific examples thereof include an alkali metal (e.g., Li, Na, K) and a fluoride thereof, an alkaline earth metal (e.g., Mg, Ca) and a fluoride thereof, gold, silver, lead, aluminum, a sodium-potassium alloy and a mixed metal thereof, a lithium-aluminum alloy and a mixed metal thereof, a magnesium-silver alloy and a mixed metal thereof, and a rare earth metal such as indium and ytterbium. Of these, materials having a work function of 4 eV or less are preferred, and aluminum, a lithium-aluminum alloy and a mixed metal thereof and a magnesium-silver alloy and a mixed metal thereof are more preferred. The cathode may be formed not only as a single layer of the above-described compound or mixture but also as a laminate structure including the compound or mixture. The thickness of the cathode may be freely decided depending on the material used, however, it is usually in the range of preferably from 10 nm to 5 µm, more preferably from 50 nm to 1 µm, still more preferably from 100 nm to 1 µm. The cathode may be prepared by an electron beam method, a sputtering method, a resistance heating evaporation method or a coating method, and a sole metal may be deposited or two or more components may be simultaneously deposited. Furthermore, a plurality of metals may be simultaneously deposited to form an alloy electrode or an alloy previously prepared may be deposited. The anode and the cathode each preferably has a low sheet resistance of hundreds of Ω/☐ or less.

The material for the light emitting layer may be any as far as it can form a layer having a function of injecting holes from the anode, hole injecting layer or hole transporting layer and at the same time injecting electrons from the cathode, electron injecting layer or electron transporting layer upon application of an electric field, a function of transferring charges injected, and a function of offering a chance such that the hole and the electron recombine and emit light. The light emitting layer preferably contains a cyclic azine compound of the present invention but other light emitting materials may be used. Examples thereof include various metal complexes including metal complexes and rare earth complexes such as benzoxazole derivative, benzimidazole derivative, benzothiazole derivative, styrylbenzene derivative, polyphenyl derivative, diphenylbutadiene derivative, tetraphenyl-butadiene derivative, naphthalimide derivative, coumarin derivative, perylene derivative, perynone derivative, oxadiazole derivative, aldazine derivative, pyralidine derivative, cyclopentadiene derivative, bisstyrylanthracene derivative, quinacridone derivative, pyrropyridine derivative, thiazolopyridine derivative, cyclopentadiene derivative, styrylamine derivative, aromatic dimethylidyne compound and 8-quinolinol derivative, and polymer compounds such as polythiophene, polyphenylene and polyphenylene-vinylene. The thickness of the light emitting layer is not particularly limited, however, it is usually in the range of preferably from 1 nm to 5 µm, more preferably from 5 nm to 1 µm, still more preferably from 10 to 500 nm.

The method for forming the light emitting layer is not particularly limited and a resistance heating evaporation method, an electron beam method, a sputtering method, a molecular lamination method, a coating method (e.g., spin coating, casting, dip coating) and an LB method are used. Of these, a resistance heating evaporation method and a coating method are preferred.

The material for the hole injecting layer and the hole transporting layer may be any as far as it has any one of a function of injecting holes from the anode, a function of transporting holes and a function of blocking electrons injected from the cathode. Specific examples thereof include electrically conductive high molecular oligomers such as carbazole derivative, triazole derivative, oxazole derivative, oxadiazole derivative, imidazole derivative, polyarylalkane derivative, pyrazoline derivative, pyrazolone derivative, phenylenediamine derivative, arylamine derivative, amino-substituted chalcone derivative, styrylanthracene derivative, fluorenone derivative, hydrazone derivative, stilbene derivative, silazane derivative, aromatic tertiary amine compound, styrylamine compound, aromatic dimethylidyne-based compound, porphyrin-based compound, polysilane-based compound, poly(N-vinylcarbazole) derivative, aniline-based copolymer, thiophene oligomer and polythiophene. The hole injecting layer and the hole transporting are not particularly limited on the thickness, however, the thickness is usually in the range of preferably from 1 nm to 5 µm, more preferably from 5 nm to 1 µm, still more preferably from 10 to 500 nm. The hole injecting layer and the hole transporting layer each may have a single layer structure comprising one or more of the above-described materials or may have a multi-layer structure comprising a plurality of layers which are the same or different in the composition.

The hole injecting layer and the hole transporting layer each is formed by a vacuum evaporation method, an LB method or a method of dissolving or dispersing the above-described hole injecting and transporting agent in a solvent and coating the solution (e.g., spin coating, casting, dip coating). In the case of the coating method, the material can be dissolved or dispersed together with a resin component. Examples of the resin component include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide resin, ethyl cellulose, vinyl acetate, ABS resin, polyurethane, melamine resin, unsaturated polyester resin, alkyd resin, epoxy resin and silicone resin.

The material for the electron injecting layer and the electron transporting layer may be any as far as it has any one of a function of injecting electrons from the cathode, a function of transporting electrons and a function of blocking holes injected from the anode. Specific examples thereof include heterocyclic tetracarboxylic acid anhydrides such as triazole derivative, oxazole derivative, oxadiazole derivative, fluorenone derivative, anthraquinodimethane derivative, anthrone derivative, diphenylquinone derivative, thiopyran dioxide derivative, carbidiimide derivative, fluorenylidenemethane derivative, distyryl-pyrazine derivative and naphthalene perylene, and various metal complexes such as metal complex of phthalocyanine derivative and 8-quinolinol derivative, and metal complex containing metal phthalocyanine, benzoxazole or benzothiazole as a ligand. The electron injecting layer and the electron transporting layer are not particularly limited on the thickness, however, the thickness is usually in the range of preferably from 1 nm to 5 $\mu$m, more preferably from 5 nm to 1 $\mu$m, still more preferably from 10 to 500 nm. The electron injecting layer and the electron transporting layer each may have a single layer structure comprising one or more of the above-described materials or may have a multi-layer structure comprising a plurality of layers which are the same or different in the composition.

The electron injecting layer and the electron transporting layer each is formed by a vacuum evaporation method, an LB method or a method of dissolving or dispersing the above-described electron injecting and transporting agent in a solvent and coating the solution (e.g., spin coating, casting, dip coating). In the case of the coating method, the material can be dissolved or dispersed together with a resin component. Examples of the resin component include those described for the hole injecting and transporting layer.

The material for the protective layer may any as far as it has a function of preventing a substance which accelerates deterioration of the device, such as moisture and oxygen, from entering the device. Specific examples thereof include metals such as In, Sn, Pb, Au, Cu, Ag, Al, Ti and Ni, metal oxides such as MgO, SiO, $SiO_2$, $Al_2O_3$, GeO, NiO, CaO, BaO, $Fe_2O_3$, $Y_2O_3$ and $TiO_2$, metal fluorides such as $MgF_2$, LiF, $AlF_3$ and $CaF_2$, polyethylene, polypropylene, polymethyl methacrylate, polyimide, polyurea, polytetrafluoroethylene, polychlorotrifluoroethylene, polydichlorodifluoroethylene, a copolymer of chlorotrifluoroethylene and dichlorodifluoroethylene, a copolymer obtained by copolymerizing a monomer mixture containing tetrafluoro-ethylene and at least one comonomer, a fluorine-containing copolymer having a cyclic structure in the copolymer main chain, a water absorptive substance having a coefficient of water absorption of 1% or more, and a moisture-proofing substance having a coefficient of water absorption of 0.1% or less.

The method for forming the protective layer is not particularly limited and, for example, a vacuum evaporation method, a sputtering method, a reactive sputtering method, an MBE (molecular beam epitaxy) method, a cluster ion beam method, an ion plating method, a plasma polymerization method (high frequency exciting ion plating method), a plasma CVD method, a laser CVD method, a thermal CVD method and a gas source CVD method may be used.

The compounds represented by formulae (1) to (4) of the present invention may be used, in addition to the use for organic EL devices, for photographic dyes, ink jet dyes, printing dyes, heat-sensitive transfer recording dyes, color filter dyes, color conversion filter dyes or medical items.

The present invention is described in greater detail below, however, the present invention should not be construed as being limited thereto.

EXAMPLE 1

A glass plate in a size of 25 mm×25 mm×0.7 mm having formed thereon a 150 nm-thick ITO film (manufactured by Tokyo Sanyo Shinku KK) was used as a transparent substrate. This transparent substrate was etched and rinsed. Thereafter, a solution obtained by dissolving 40 mg of poly(N-vinylcarbazole), 12 mg of PBD (2-(4-biphenylyl)-5-(4-tert-butylphenyl)-1,3,4-oxadiazole) and 0.5 mg of a compound shown in Table 1 in 3 ml of 1,2-dichloroethane was spin-coated on the rinsed ITO substrate. The organic thin film produced had a thickness of about 120 nm. On the organic thin film, a patterned mask (mask having an emission area of 5 mm×5 mm) was provided. Then, in an evaporation apparatus, magnesium : silver (10:1) were co-deposited to have a thickness of 50 nm and further silver was deposited to have a thickness of 50 nm.

A dc constant voltage was applied to the EL device obtained to cause light emission using a source measure unit Model 2400 (manufactured by Toyo Technica KK) and the luminance and emission wavelength thereof were determined by a luminance meter BM-8 (manufactured by Topcon KK) and a spectrum analyzer PMA-11 (manufactured by Hamamatsu Photonics KK), respectively. The results obtained are shown in Table 1.

TABLE 1

| Device No. | Compound | Emission Luminance (cd/m$^2$) | Driving Voltage (V) | Emission Wavelength, $\lambda$max (nm) | CIE Chromaticity Coordinates (x, y) | Remarks |
|---|---|---|---|---|---|---|
| Comparative Compound | | | | | | |
| 101 | A | 70 | 16 | 595 | (0.50, 0.50) | Comparison |
| 102 | B | 25 | 18 | 603 | (0.59, 0.40) | " |
| Compound of the Invention | | | | | | |
| 103 | 2-1 | 100 | 15 | 615 | (0.62, 0.35) | Invention |
| 104 | 2-2 | 245 | 13 | 605 | (0.60, 0.39) | " |
| 105 | 2-19 | 200 | 15 | 615 | (0.60, 0.37) | " |
| 106 | 2-26 | 168 | 15 | 620 | (0.62, 0.36) | " |
| 107 | 2-28 | 260 | 14 | 618 | (0.61, 0.38) | " |

TABLE 1-continued

| Device No. | Compound | Emission Luminance (cd/m²) | Driving Voltage (V) | Emission Wavelength, λmax (nm) | CIE Chromaticity Coordinates (x, y) | Remarks |
|---|---|---|---|---|---|---|
| 108 | 2-34 | 210 | 14 | 612 | (0.60, 0.37) | " |
| 109 | 2-39 | 280 | 14 | 610 | (0.59, 0.37) | " |

Comparative Compound A:

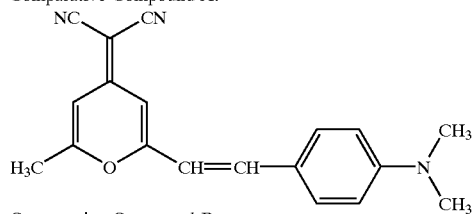

Comparative Compound B:

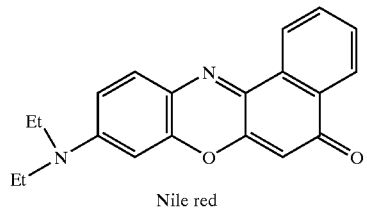

Nile red

As apparent from the results in Table 1, in the case of devices using the compound of the present invention, low voltage driving and high luminance light emission could be attained as compared with the devices using a comparative compound even in the coating method where the emission luminance is usually low, and at the same time, red light emission in high color purity was exhibited.

EXAMPLE 2

In the same manner as in Example 1, an ITO substrate was etched and rinsed and thereon TPD (N,N'-bis(3-methylphenyl)-N,N'-diphenylbenzidine), a compound shown in Table 2 and 2,5-bis(1-naphthyl)-1,3,4-oxadiazole were in sequence deposited in a vacuum of from $10^{-5}$ to $10^{-6}$ Torr under the condition of the substrate temperature being room temperature to have a thickness of about 40 nm, about 20 nm and about 40 nm, respectively. Thereafter, a cathode was deposited in the same manner as in Example 1 and the devices were evaluated. The results obtained are shown in As apparent from the results in Table 2, in the case of devices using the compound of the present invention, high luminance light emission could be attained as compared with the devices using a comparative compound and at the same time, red light emission in high color purity was exhibited.

EXAMPLE 3

In the same manner as in Example 1, an ITO substrate was etched and rinsed. On the rinsed substrate, TPD was deposited to have a thickness of about 40 nm and then a compound shown in Table 3 and Alq (tris(8-hydroxy-quinolinato) aluminum) were co-deposited at a deposition rate of 0.04 Å/sec and 4 Å/sec, respectively, to have a thickness of about 60 nm. Thereafter, a cathode was deposited in the same manner as in Example 1 and the devices were evaluated. The results obtained are shown in Table 3.

TABLE 2

| Device No. | Compound | Emission Luminance (cd/m²) | Driving Voltage (V) | Emission Wavelength, λmax (nm) | CIE Chromaticity Coordinates (x,y) | Remarks |
|---|---|---|---|---|---|---|
| Comparative Compound | | | | | | |
| 101 | A | 250 | 16 | 610 | (0.54, 0.48) | Comparison |
| 102 | B | 110 | 16 | 635 | (0.64, 0.32) | " |
| Compound of the Invention | | | | | | |
| 103 | 2-1 | 200 | 15 | 640 | (0.66, 0.32) | Invention |
| 104 | 2-2 | 310 | 13 | 635 | (0.65, 0.33) | " |
| 106 | 2-26 | 210 | 15 | 640 | (0.66, 0.31) | " |
| 108 | 2-34 | 280 | 14 | 635 | (0.64, 0.30) | " |

TABLE 3

| Device No. | Compound | Emission Luminance (cd/m²) | Driving Voltage (V) | Emission Wavelength, λmax (nm) | CIE Chromaticity Coordinates (x,y) | Dark Spot | Remarks |
|---|---|---|---|---|---|---|---|
| Comparative Compound | | | | | | | |
| 101 | A | 250 | 15 | 605 | (0.51, 0.48) | Δ | Comparison |
| 102 | B | 150 | 17 | 635 | (0.64, 0.33) | x | " |
| Compound of the Invention | | | | | | | |
| 103 | 2-1 | 900 | 17 | 637 | (0.65, 0.32) | ○ | Invention |
| 104 | 2-2 | 1050 | 14 | 633 | (0.64, 0.33) | ○ | " |
| 106 | 2-26 | 360 | 16 | 640 | (0.66, 0.31) | Δ | " |
| 108 | 2-34 | 760 | 14 | 630 | (0.60, 0.30) | ○ | " |

*○: Dark spots cannot be visually confirmed.
Δ: Few dark spots.
x: Many dark spots.

As apparent from the results in Table 3, in the case of devices using the compound of the present invention, high luminance light emission could be attained as compared with the devices using a comparative compound also in the evaporation method and doped system, color purity was high, red light emission excellent in the face state was exhibited, and durability was superior.

EXAMPLE 4

In the same manner as in Example 1, an ITO substrate was etched and rinsed. On the rinsed substrate, TPD was deposited to have a thickness of about 40 nm and then Compound 2-2 was deposited to have a thickness of about 60 nm. Thereafter, a cathode was deposited in the same manner as in Example 1.

As a result of evaluation, the device fabricated exhibited a luminance of 120 cd/m² at 11 V. Furthermore, red light emission in high color purity such that λmax=630 nm and CIE chromaticity (x,y)=(0.67, 0.32) was observed. Thus, the compound of the present invention was verified to be effective as an electron injecting and transporting agent and at the same time, as an emitter.

EXAMPLE 5

In the same manner as in Example 1, an ITO substrate was etched and rinsed, and thereon, a solution obtained by dissolving 40 mg of poly(N-vinylcarbazole), 12 mg of 2,5-bis(1-naphthyl)-1,3,4-oxdiazole, 10 mg of tetrapheyl-butadiene, 0.5 mg of DCM and 0.1 mg of Compound 2-1 of the present invention in 3 ml of 1,2-dichloroethane was spin-coated. Thereafter, a cathode was deposited in the same manner as in Example 1.

Then, a dc voltage was applied to the device obtained using the ITO electrode as an anode and the Mg:Ag electrode as a cathode to examine the light emission properties. As a result, white light emission (luminance: 1,420 cd/m²) at (x,y)=(0.34, 0.36) on the CIE chromaticity diagram was obtained at 15V. Thus, the device was verified to be effective for white light emission.

EXAMPLE 6

A glass plate in a size of 25 mm×25 mm×0.7 mm having formed thereon a 150 nm-thick ITO film (manufactured by Tokyo Sanyo Shinku KK) was used as a transparent substrate. This transparent substrate was etched and rinsed. Thereafter, a solution obtained by dissolving 40 mg of poly(N-vinylcarbazole), 12 mg of PBD (2-(4-biphenylyl)-5-(4-tert-butylphenyl)-1,3,4-oxadiazole) and 1.0 mg of a compound shown in Table 4 in 3 ml of 1,2-dichloroethane was spin-coated on the rinsed ITO substrate. The organic thin film produced had a thickness of about 120 nm. On the organic thin film, a patterned mask was provided. Then, in an evaporation apparatus, magnesium : silver (10:1) were co-deposited to have a thickness of 250 nm and further silver was deposited to have a thickness of 300 nm.

A dc constant voltage was applied to the EL device obtained to cause light emission using a source measure unit Model 2400 (manufactured by Toyo Technica KK) and the luminance and emission wavelength thereof were determined by a luminance meter BM-8 (manufactured by Topcon KK) and a spectrum analyzer PMA-11 (manufactured by Hamamatsu Photonics KK), respectively. The results obtained are shown in Table 4.

TABLE 4

| Device No. | Compound | Emission Luminance (cd/m²) | Driving Voltage (V) | Emission Wavelength, λmax (nm) | CIE Chromaticity Coordinates (x, y) | Dark Spot | Remarks |
|---|---|---|---|---|---|---|---|
| Comparative Compound | | | | | | | |
| 101 | A | 200 | 16 | 595 | (0.50, 0.50) | Δ | Comparison |
| 102 | B | 110 | 16 | 590 | (0.52, 0.47) | x | " |

TABLE 4-continued

| Device No. | Compound | Emission Luminance (cd/m²) | Driving Voltage (V) | Emission Wave-length, λmax (nm) | CIE Chromaticity Coordinates (x, y) | Dark Spot | Remarks |
|---|---|---|---|---|---|---|---|
| Compound of the Invention | | | | | | | |
| 103 | 2-44 | 220 | 14 | 600 | (0.57, 0.46) | ○ | Invention |
| 104 | 2-45 | 190 | 16 | 595 | (0.55, 0.50) | Δ | " |
| 105 | 2-46 | 220 | 16 | 600 | (0.58, 0.43) | Δ | " |
| 106 | 2-48 | 230 | 15 | 605 | (0.53, 0.48) | ○ | " |
| 107 | 1-3 | 250 | 16 | 625 | (0.61, 0.35) | Δ | " |
| 108 | 1-7 | 190 | 16 | 630 | (0.62, 0.32) | Δ | " |
| 109 | 2-56 | 260 | 15 | 630 | (0.63, 0.31) | ○ | " |

*○: Dark spots cannot be visually confirmed.
Δ: Few dark spots.
x: Many dark spots.

Comparative Compound A:

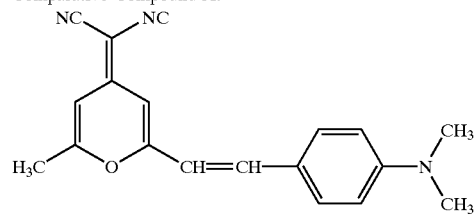

Comparative Compound B:

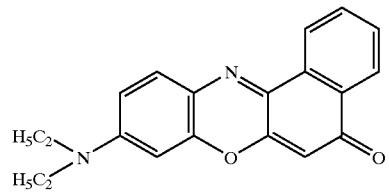

Using Nile red as a comparative compound, a maximum luminance of 110 cd/m² was exhibited at 16 V, the λmax of light emission was 590 nm and dark spots were visually observed on the emission surface.

As apparent from the results in Table 4, in the case of devices using the compound of the present invention, low voltage driving and high luminance light emission could be attained as compared with the devices using a comparative compound even in the coating method where the emission luminance is usually low, and at the same time, red light emission in high color purity was exhibited. Furthermore, the durability was superior.

EXAMPLE 7

In the same manner as in Example 6, an ITO substrate was etched and rinsed and thereon TPD (N,N'-bis(3-methylphenyl)-N,N'-diphenylbenzidine), a compound shown in Table 5 and 2,5-bis(1-naphthyl)-1,3,4-oxadiazole were in sequence deposited in a vacuum of from $10^{-5}$ to $10^{-6}$ Torr under the condition of the substrate temperature being room temperature to have a thickness of about 40 nm, about 20 nm and about 40 nm, respectively. Thereafter, a cathode was deposited in the same manner as in Example 1 and the devices were evaluated. The results obtained are shown in Table 5.

TABLE 5

| Device No. | Compound | Emission Luminance (cd/m²) | Driving Voltage (V) | Emission Wavelength, λmax (nm) | CIE Chromaticity Coordinates (x,y) | Remarks |
|---|---|---|---|---|---|---|
| Comparative Compound | | | | | | |
| 201 | A | 250 | 16 | 610 | (0.54, 0.48) | Comparison |
| 202 | B | 110 | 16 | 635 | (0.64, 0.32) | " |

TABLE 5-continued

| Device No. | Compound | Emission Luminance (cd/m$^2$) | Driving Voltage (V) | Emission Wavelength, λmax (nm) | CIE Chromaticity Coordinates (x,y) | Remarks |
|---|---|---|---|---|---|---|
| Compound of the Invention | | | | | | |
| 203 | 2-56 | 300 | 15 | 635 | (0.65, 0.33) | Invention |
| 204 | 2-58 | 190 | 15 | 640 | (0.66, 0.32) | " |
| 206 | 2-55 | 220 | 16 | 625 | (0.64, 0.32) | " |
| 208 | 2-72 | 250 | 16 | 630 | (0.65, 0.33) | " |

As apparent from the results in Table 5, in the devices using the compound of the present invention, high luminance light emission could be attained as compared with the devices using a comparative compound also in the evaporation method and at the same time, red light emission in high color purity was exhibited.

EXAMPLE 8

In the same manner as in Example 6, an ITO substrate was etched and rinsed. On the rinsed substrate, TPD was deposited to have a thickness of about 40 nm and then a compound shown in Table 6 and Alq (tris(8-hydroxy-quinolinato) aluminum) were co-deposited at a deposition rate of 0.04 Å/sec and 4 Å/sec, respectively, to have a thickness of about 60 nm. Thereafter, a cathode was deposited in the same manner as in Example 6 and the devices were evaluated. The results obtained are shown in Table 6.

TABLE 6

| Device No. | Compound | Emission Luminance (cd/m$^2$) | Driving Voltage (V) | Emission Wavelength, λmax (nm) | CIE Chromaticity Coordinates (x,y) | Dark Spot | Remarks |
|---|---|---|---|---|---|---|---|
| Comparative Compound | | | | | | | |
| 301 | A | 250 | 15 | 605 | (0.51, 0.48) | Δ | Comparison |
| 302 | B | 150 | 17 | 635 | (0.64, 0.33) | x | " |
| Compound of the Invention | | | | | | | |
| 303 | 2-56 | 900 | 16 | 637 | (0.65, 0.32) | ○ | Invention |
| 304 | 2-58 | 1050 | 14 | 633 | (0.64, 0.33) | ○ | " |
| 306 | 2-55 | 360 | 16 | 640 | (0.66, 0.31) | Δ | " |
| 308 | 2-72 | 760 | 14 | 630 | (0.60, 0.30) | ○ | " |

*○: Dark spots cannot be visually confirmed.
Δ: Few dark spots.
x: Many dark spots.

As apparent from the results in Table 6, in the case of devices using the compound of the present invention, high luminance light emission could be attained as compared with the devices using a comparative compound also in the evaporation method and doped system, color purity was high, red light emission excellent in the face state was exhibited, and durability was superior.

EXAMPLE 9

In the same manner as in Example 6, an ITO substrate was etched and rinsed. On the rinsed substrate, TPD was deposited to have a thickness of about 40 nm and then Compound 2-58 was deposited to have a thickness of about 60 nm. Thereafter, a cathode was deposited in the same manner as in Example 6.

As a result of evaluation, the device fabricated exhibited a luminance of 110 cd/m$^2$ at 12 V. Furthermore, red light emission in high color purity such that λmax=625 nm and CIE chromaticity (x,y)=(0.66, 0.32) was observed. Thus, the compound of the present invention was verified to be effective as an electron injecting and transporting agent and at the same time, as an emitter.

EXAMPLE 10

In the same manner as in Example 6, an ITO substrate was etched and rinsed, and thereon, a solution obtained by dissolving 40 mg of poly(N-vinylcarbazole), 12 mg of 2,5-bis(1-naphthyl)-1,3,4-oxadiazole, 10 mg of tetraphenylbutadiene, 0.5 mg of DCM and 0.1 mg of Compound 2-58 of the present invention in 3 ml of 1,3-dichloroethane was spin-coated. Thereafter, a cathode was deposited in the same manner as in Example 6.

Then, a dc voltage was applied to the device obtained using the ITO electrode as an anode and the Mg:Ag electrode as a cathode to examine the light emission properties. As a result, white light emission (luminance: 1,280 cd/m$^2$) at (x,y)=(0.36, 0.35) on the CIE chromaticity diagram was obtained at 16 V. Thus, the device was verified to be effective for white light emission.

COMPARATIVE EXAMPLE 40 mg of polyvinylcarbazole, 12 mg of PBD (p-t-butylphenylbiphenyloxadiazole) and 1 mg of tetraphenylbutadiene were dissolved in 3 ml of dichloroethane and the solution obtained was spin-coated on a rinsed ITO substrate. The organic thin film produced had a thickness of about 120 nm. A patterned mask was provided on the organic thin film. Then, in an evaporation apparatus, magnesium : silver (10:1) were co-deposited to have a thickness of 250 nm and then silver was deposited thereon to have a thickness of 300 nm.

A dc constant voltage was applied to the EL device to cause light emission using a source measure unit Model 2400 (manufactured by Toyo Technica KK) and the luminance and emission wavelength thereof were determined by a luminance meter BM-8 (manufactured by Topcon KK) and a spectrum analyzer PMA-11 (manufactured by Hamamatsu Photonics KK), respectively. As a result, a maximum luminance of 280 cd/m$^2$ was exhibited at 12 V and the $\lambda$max of light emission was 450 nm. The device fabricated was left standing for 5 hours and then made to emit light. Then, dark spots were visually observed on the emission surface. The generation of dark spots on the emission surface reveals that the device is deteriorated.

EXAMPLE 11

An EL device was fabricated in the same manner except for using the cyclic azine dye (3–1) synthesized above in place of tetraphenylbutadiene used in the Comparative Example, and evaluated. As a result, light emission of $\lambda$max=480 nm was obtained and luminance of 520 cd/m$^2$ was achieved at 14 V. No dark spot was visually observed on the light emission surface.

EXAMPLE 12

An EL device was fabricated in the same manner except for using the cyclic azine dye (3–5) synthesized above in place of tetraphenylbutadiene used in the Comparative Example, and evaluated. As a result, light emission of $\lambda$max=485 nm was obtained and luminance of 435 cd/m$^2$ was achieved at 15 V. No dark spot was visually observed on the light emission surface.

EXAMPLE 13

An EL device was fabricated in the same manner except for using the cyclic azine dye (3–13) synthesized above in place of tetraphenylbutadiene used in the Comparative Example, and evaluated. As a result, light emission of $\lambda$max=465 nm was obtained and luminance of 290 cd/m$^2$ was achieved at 16 V. No dark spot was visually observed on the light emission surface.

It is apparent from the results in the Examples above that when a cyclic azine dye specified in the present invention is used, a blue-green emissive EL device capable of emitting light at a wavelength in the blue-green area can be fabricated and the cyclic azine dye has excellent durability.

While the invention has been described in detail and with reference to specific embodiments thereof, it will be apparent to one skilled in the art that various changes and modifications can be made therein without departing from the spirit and scope thereof.

What is claimed is:

1. An organic electroluminescence device comprising at least one organic thin film between electrodes, which contains at least one compound represented by the following formula (1):

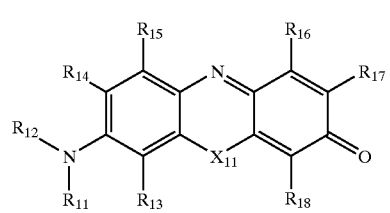

wherein $X_{11}$ represents a sulfur atom or N—$R_{19}$, and $R_{11}$ to $R_{18}$ and $R_{19}$, which may be the same or different, each represents a hydrogen atom or a substituent, provided that $R_{16}$ and $R_{17}$ are not combined to form an aromatic ring.

2. An organic electroluminescence device comprising a pair of electrodes having formed therebetween a light emitting layer or a plurality of organic compound thin films including a light emitting layer, wherein at least one layer is a layer comprising a polymer having dispersed therein a compound represented by formula (1):

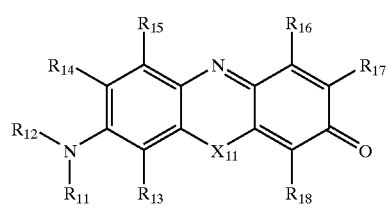

wherein $X_{11}$ represents a sulfur atom or N—$R_{19}$, and $R_{11}$ to $R_{18}$ and $R_{19}$, which may be the same or different, each represents a hydrogen atom or a substituent, provided that $R_{16}$ and $R_{17}$ are not combined to form an aromatic ring.

3. An organic electroluminescence device comprising a pair of electrodes having formed therebetween a light emitting layer or a plurality of organic compound thin films including a light emitting layer, wherein at least one layer is a layer formed by coating a compound represented by formula (1) or a material containing the compound:

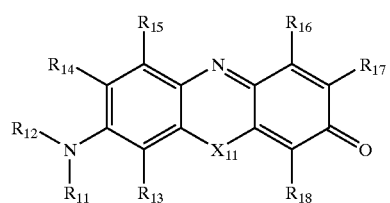

wherein $X_{11}$ represents a sulfur atom or N—$R_{19}$, and $R_{11}$ to $R_{18}$ and $R_{19}$, which may be the same or different, each represents a hydrogen atom or a substituent, provided that $R_{16}$ and $R_{17}$ are not combined to form an aromatic ring.

* * * * *